US011453910B2

United States Patent
Huber

(10) Patent No.: US 11,453,910 B2
(45) Date of Patent: Sep. 27, 2022

(54) CONTROLLING FLUORESCENT SIGNAL COMPOSITION IN OPTICALLY-BASED NANOPORE SEQUENCING

(71) Applicant: Quantapore, Inc., South San Francisco, CA (US)

(72) Inventor: Martin Huber, Menlo Park, CA (US)

(73) Assignee: Quantapore, Inc., South San Francisco, CA (US)

( * ) Notice: Subject to any disclaimer, the term of this patent is extended or adjusted under 35 U.S.C. 154(b) by 531 days.

(21) Appl. No.: 16/330,357

(22) PCT Filed: Oct. 5, 2017

(86) PCT No.: PCT/US2017/055435
§ 371 (c)(1),
(2) Date: Mar. 4, 2019

(87) PCT Pub. No.: WO2018/071273
PCT Pub. Date: Apr. 19, 2018

(65) Prior Publication Data
US 2021/0285928 A1  Sep. 16, 2021

Related U.S. Application Data

(60) Provisional application No. 62/406,210, filed on Oct. 10, 2016.

(51) Int. Cl.
*C12Q 1/6869* (2018.01)
*G01N 33/487* (2006.01)

(52) U.S. Cl.
CPC ..... *C12Q 1/6869* (2013.01); *G01N 33/48721* (2013.01)

(58) Field of Classification Search
None
See application file for complete search history.

(56) References Cited

U.S. PATENT DOCUMENTS

2016/0115531 A1   4/2016 Huber et al.

FOREIGN PATENT DOCUMENTS

WO   WO 2018/071273   4/2018

OTHER PUBLICATIONS

Lichtman et al. Fluorescence microscopy. Nature Methods 2(12):910-919. (Year: 2005).*

(Continued)

*Primary Examiner* — Samuel C Woolwine
(74) *Attorney, Agent, or Firm* — Stephen C. Macevicz; Vince M. Powers; Levine Bagade Han LLP

(57) ABSTRACT

The invention is directed to optically based methods for nanopore sequencing of polynucleotides which comprise steps of (i) translocating a polynucleotide through a bore of a nanopore at a translocation speed, wherein nucleotides of the polynucleotide are labeled with fluorescent labels such that in free solution fluorescent labels of nucleotides are substantially quenched and wherein fluorescent labels within the bore are constrained such that substantially no detectable fluorescent signal is generated therein; (ii) exciting the fluorescent label of each nucleotide upon exiting the nanopore and prior to quenching with a preceding mutually quenching fluorescent label or a quenching agent; (iii) measuring a fluorescent signal generated by fluorescent labels exiting the nanopore, wherein the translocation speed is selected so that the measured fluorescent signal comprises fluorescence from substantially a single fluorescent label; and (iv) determining a nucleotide sequence of the polynucleotide from a sequence of measured fluorescent signals.

11 Claims, 11 Drawing Sheets

Specification includes a Sequence Listing.

(56) References Cited

OTHER PUBLICATIONS

Fologea, et al. "Slowing DNA Translocation in a Solid State Nanopore," *Nano Letters,* 5 (9), pp. 1734-1737, Sep. 2005.

* cited by examiner

SEQUENCE LISTING

```
<160> NUMBER OF SEQ ID NOS: 1

<210> SEQ ID NO 1
<211> LENGTH: 25
<212> TYPE: DNA
<213> ORGANISM: Artificial Sequence
<220> FEATURE:
<223> OTHER INFORMATION: The sequence is synthesized.

<400> SEQUENCE: 1
accgtttaaa ggtttccccg tcgta                                        25
```

CONTROLLING FLUORESCENT SIGNAL COMPOSITION IN OPTICALLY-BASED NANOPORE SEQUENCING

CROSS-REFERENCE TO RELATED APPLICATIONS AND SEQUENCE LISTING

This application claims benefit of priority to U.S. Provisional Application No. 62/406,210, filed Oct. 10, 2016, which is incorporated herewith in its entirety. A Sequence Listing is being provided in electronic format. The Sequence Listing is provided as a file entitled 02_QNTTPNZ02100_20220420 sequence listing ST25.txt, created Apr. 19, 2022, which is 530 bytes in size. The information in the electronic format of the Sequence Listing is incorporated herein by reference in its entirety.

BACKGROUND

Huber and colleagues discovered that by judicious selection of nanopores fluorescent signals from fluorophore-labeled nucleotides of a translocating polynucleotide may be rendered undetectable and that upon exit from the nanopore may regain detectability. This phenomena may be exploited practically in connection with another phenomena; namely, use of quenching agents or mutually quenching fluorescent labels on a polynucleotide, which in free solution quench one another. Application of these phenomena lead to a polynucleotide sequencing approach wherein nanopore-exiting nucleotides freed from nanopore-imposed constraints are capable of excitation and emission of a detectable signal for an interval just prior to quenching by a fluorescent label of a nucleotide that preceded it through the nanopore. Huber et al, U.S. patent publication 2016/0076091 and Huber, U.S. patent publication 2016/0122812. The duration of the interval and translocation speed, among other factors, determine how many labels may contribute fluorescence to measured signals of each signal collection cycle.

Optically based nanopore sequencing would be advanced and base calling greatly simplified if these system parameters could be controlled so that measured fluorescent signals of each signal collection cycle consisted of fluorescence substantially from single labels.

SUMMARY OF THE INVENTION

The present invention is directed to methods, kits and systems for optical detection and analysis of polymers, such as polynucleotides, in microfluidic and/or nanofluidic devices; in particular, the invention includes methods and systems using nanopores for determining nucleotide sequences of nucleic acids.

In some embodiments, the invention is directed to a method for determining a nucleotide sequence of a polynucleotide comprising the steps of: (a) translocating a polynucleotide through a bore of a nanopore at a translocation speed, wherein nucleotides of the polynucleotide are labeled with fluorescent labels such that in free solution fluorescent labels of nucleotides are substantially quenched and wherein fluorescent labels within the bore are constrained such that substantially no detectable fluorescent signal is generated therein; (b) exciting the fluorescent label of each nucleotide upon exiting the nanopore and prior to quenching with a preceding mutually quenching fluorescent label or a quenching agent; (c) measuring a fluorescent signal generated by fluorescent labels exiting the nanopore, wherein the translocation speed is selected so that the measured fluorescent signal comprises fluorescence from substantially a single fluorescent label; and (d) determining a nucleotide sequence of the polynucleotide from a sequence of measured fluorescent signals.

The present invention is exemplified in a number of implementations and applications, some of which are summarized below and throughout the specification.

DETAILED DESCRIPTION OF THE INVENTION

Figure 1A:
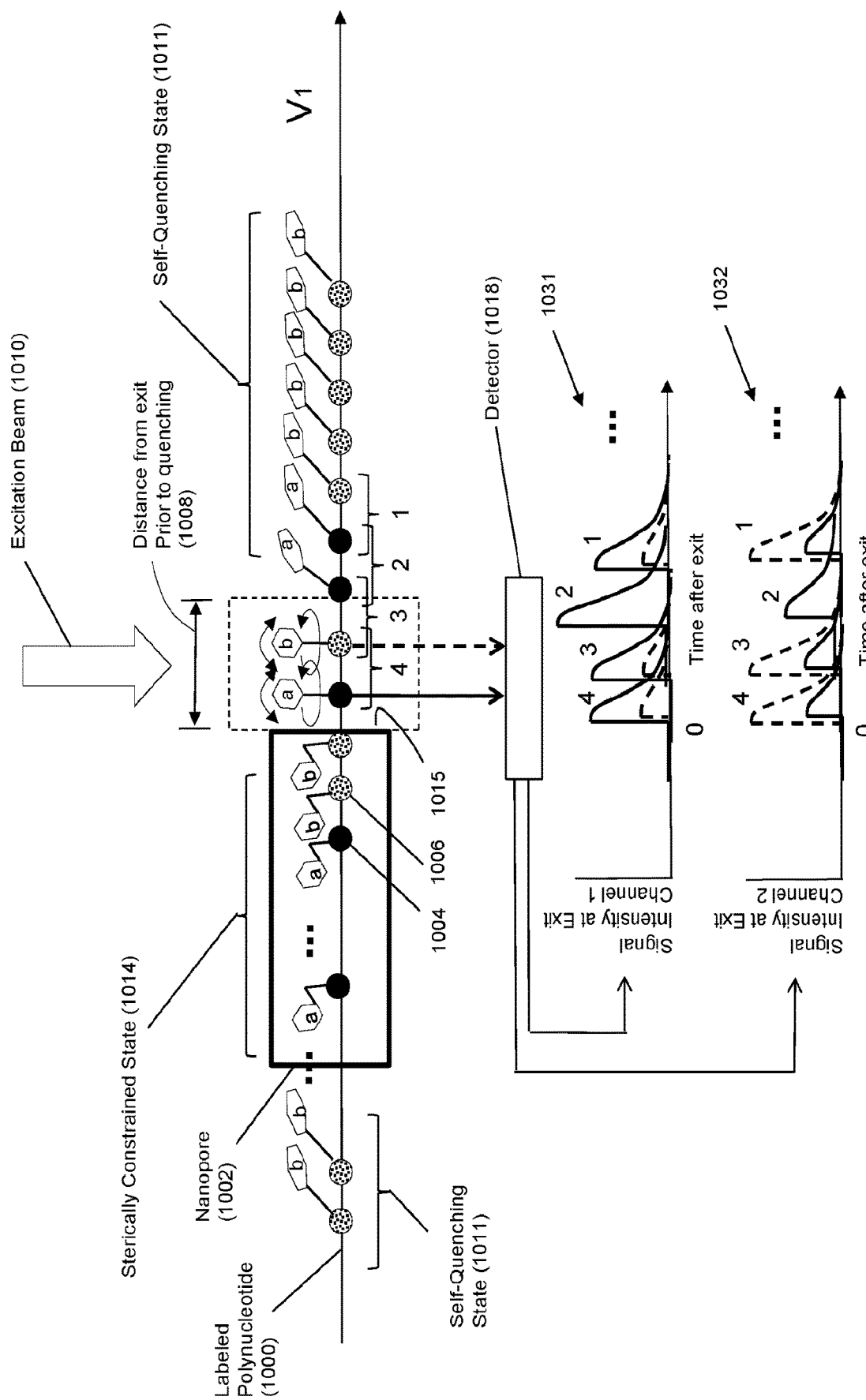
FIGS. 1A-1B illustrate labeled polynucleotides translocating nanopores at different speeds and the effect the different translocation speeds have on measured fluorescent signals.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention. For example, particular nanopore types and numbers, particular labels, FRET pairs, detection schemes, fabrication approaches of the invention are shown for purposes of illustration. It should be appreciated, however, that the disclosure is not intended to be limiting in this respect, as other types of nanopores, arrays of nanopores, and other fabrication technologies may be utilized to implement various aspects of the systems discussed herein. Guidance for aspects of the invention is found in many available references and treatises well known to those with ordinary skill in the art, including, for example, Cao, Nanostructures & Nanomaterials (Imperial College Press, 2004); Levinson, Principles of Lithography, Second Edition (SPIE Press, 2005); Doering and Nishi, Editors, Handbook of Semiconductor Manufacturing Technology, Second Edition (CRC Press, 2007); Sawyer et al, Electrochemistry for Chemists, $2^{nd}$ edition (Wiley Interscience, 1995); Bard and Faulkner, Electrochemical Methods: Fundamentals and Applications, $2^{nd}$ edition (Wiley, 2000); Lakowicz, Principles of Fluorescence Spectroscopy, $3^{rd}$ edition (Springer, 2006); Hermanson, Bioconjugate Techniques, Second Edition (Academic Press, 2008); and the like, which relevant parts are hereby incorporated by reference.

In one aspect, the invention relates to the use of nanopores, fluorescent quenching, and fluorescent signaling to sequentially identify nucleotides of fluorescently labeled polynucleotide analytes. Such analysis of polynucleotide analytes may be carried out on single polynucleotides or on pluralities of polynucleotides in parallel at the same time, for example, by using an array of nanopores. In some embodiments, nucleotides are labeled with fluorescent labels that are capable of at least three states while attached to a polynucleotide: (i) A substantially quenched state wherein fluorescence of an attached fluorescent label is quenched by a fluorescent label on an immediately adjacent monomer or by interaction with a quenching agent; for example, a fluorescent label attached to a polynucleotide in accordance with the invention is substantially quenched when the labeled polynucleotide is free in conventional aqueous solutions or buffers for studying and manipulating the polynucleotide. (ii) A sterically constrained state while a labeled polynucleotide is translocating through a nanopore such that the free-solution movements or alignments of attached fluorescent labels are disrupted or limited so that there is little or no detectable fluorescent signal generated from the fluorescent label. (iii) A transition state wherein fluorescent labels attached to a polynucleotide transition from the sterically constrained state to a quenched state as the nucleotide of the fluorescent label exits the nanopore (during a "transition interval" or "interval"). In part, the invention is an application of the discovery that during the transition interval a fluorescent label (on an otherwise substantially fully labeled and self-quenched or quenched polynucleotide) is capable of generating a detectable fluorescent signal and that the number of exiting labels contributing to a measured signal may be (at least in part) controlled by controlling the translocation speed of the labeled polynucleotide. If translocation speed (e.g. nucleotides exiting a nanopore per msec) is higher than the transition rate (from signal-capable to quenched, i.e. the quenching rate), then measured fluorescent signals, or signal samples, may contain contributions from more than one label. This circumstance makes signal analysis more difficult and sequence determination possibly less accurate. In accordance with some embodiments, this problem may be ameliorated by adjusting translocation speed, for example by reducing translocation speed, so that substantially only one fluorescent label at a time contributes fluorescence to a measured fluorescent signal.

Without the intention of being limited by any theory underlying this discovery, it is believed that the fluorescent signal generated during the transition interval is due to the presence of one or more freely rotatable dipoles of the fluorescent labels that emerged from a nanopore, which renders the fluorescent labels capable of generating a fluorescent signal, for example, after direct excitation or via excitation via FRET. In some embodiments, the polynucleotide is a single stranded polynucleotide, such as, DNA or RNA, but especially a single stranded DNA. In some embodiments, the invention includes a method for determining a nucleotide sequence of a polynucleotide by recording signals generated by fluorescent labels as they exit a nanopore one at a time as a polynucleotide translocates through the nanopore. A translocation speed is selected to maximize the likelihood that measured fluorescent signals comprise fluorescence from substantially only a single label, wherein such selection may be made either by real-time adjustment of parameters controllable during operation (such as the voltage across the nanopores, temperature, or the like) or by predetermined instrument set-up (e.g. reaction buffer viscosity, ion concentration, or the like). Upon exit, each attached fluorescent label transitions during a transition interval from a constrained state in the nanopore to a quenched state on the polynucleotide in free solution. During the transition interval the label is capable of generating a fluorescent signal which can be measured. In other words, in some embodiments, a step of the method of the invention comprises exciting each fluorescent label as it is transitioning from a constrained state in the nanopore to a quenched state on the polymer in free solution. As mentioned above, during this transition interval or period a fluorescent label is capable of emitting a detectable fluorescent signal indicative of the nucleotide to which it is attached.

In some embodiments, "substantially quenched" as used above means a fluorescent label generates a fluorescent signal at least thirty percent reduced from a signal generated under the same conditions, but without adjacent mutually quenching labels. In some embodiments, "substantially quenched" as used above means a fluorescent label generates a fluorescent signal at least fifty percent reduced from a signal generated under the same conditions, but without adjacent mutually quenching labels.

Figure 1B:
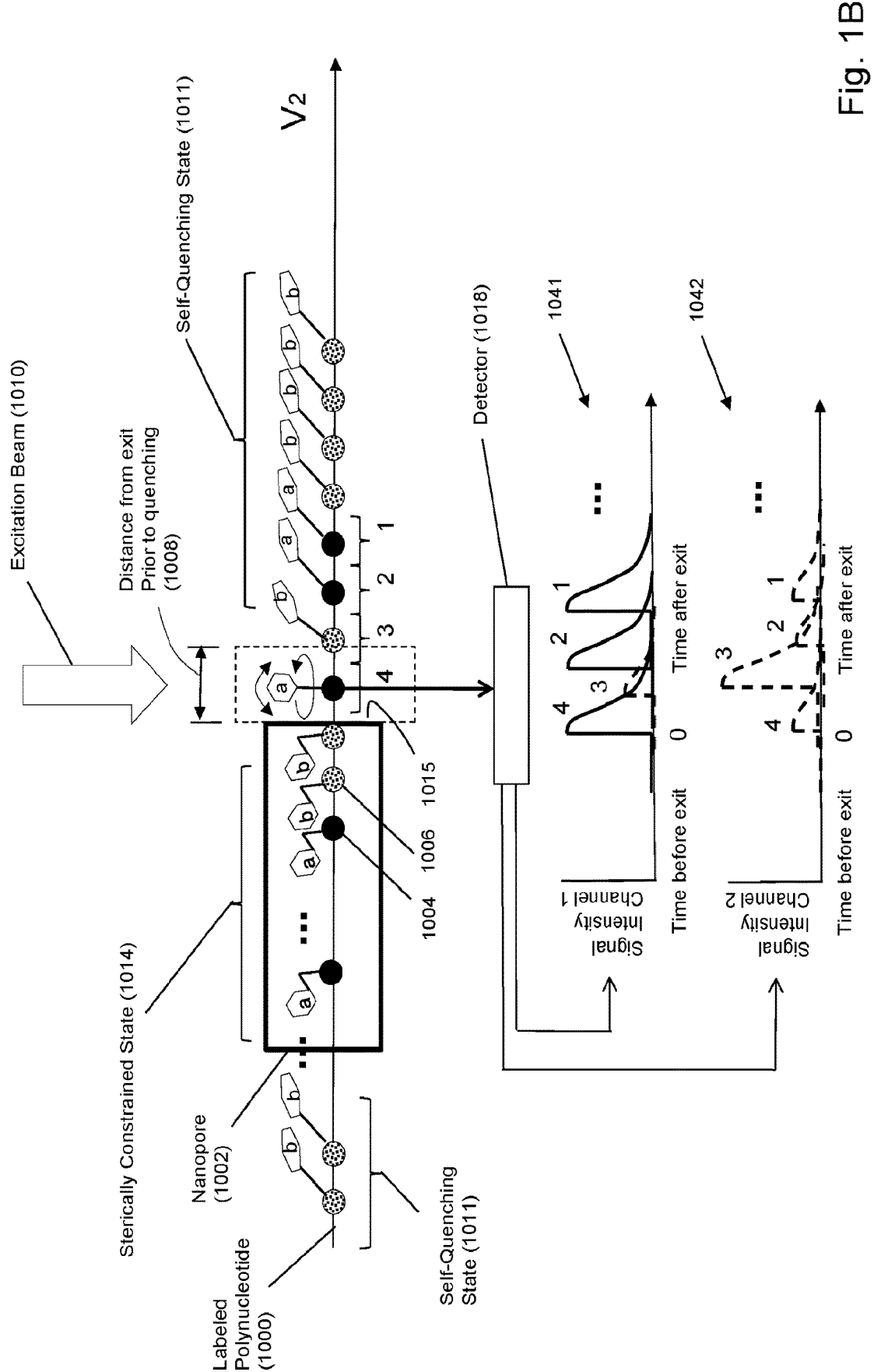

The above concepts are illustrated in FIGS. 1A-1B, which diagrammatically show labeled polynucleotide (1000) translocating through nanopore (1002). Labeled polynucleotide (1000) comprises two labels "a" and "b" (for example, which may correspond to dC being labeled with "a" and dA, dG and dT being labeled with "b", or the like). Labels of nucleotides free of nanopore (1002) are quenched, either by interaction with other labels (1011) or by action of quenching agents (not shown). Labels of nucleotides inside of nanopore (1002) are constrained and/or oriented (1014) so that they produce no detectable signal during all or part of their transit through the nanopore. As nucleotides of labeled polynucleotide (1000) emerge from exit (1015) of nanopore (1002) they become capable of being excited by excitation beam (1010) and generating a detectable signal for an interval prior to being quenched. If translocation speed $V_1$ is high then the distance (1008) traveled by a nucleotide prior to quenching may exceed the inter-nucleotide distance of polynucleotide (1000) so that more than one label (shown in FIG. 1A) contributes fluorescence to a fluorescent signal collected by detector (1018), i.e. a measured fluorescent signal. If translocation speed $V_2$ is low then the distance (1008) traveled by a nucleotide prior to quenching may approximately equal or be less than the inter-nucleotide distance of polynucleotide (1000) so that no more than one label (shown in FIG. 1B) contributes fluorescence to a fluorescent signal collected by detector (1018), i.e. a measured fluorescent signal. Since the distance between adjacent labels is below the diffraction limit of excitation light (1010) no information is obtained about the ordering of the labels, although there are approaches to deduce such information using specialized algorithms, e.g. Anderson et al, U.S. provisional patent application 62/322,343; Timp et al, Biophys. J., 102: L37-L39 (2012); Carson et al, Nanotechnology, 26: 074004 (2015). In the case of optical detection using fluorescent labels with distinct emission bands, measured fluorescent signals may be separated into two or more channels, e.g. using bandpass filters, in order to assess the relative contributions of fluorescence from multiple labels. However, as the number of fluorescent labels contributing fluorescence increases, e.g. 3, 4, or more, the difficulty in determining a correct ordering of nucleotides increases. The signal intensities for two channels, e.g. corresponding to emission maxima of two fluorescent labels, is illustrated in FIG. 1A (1031 and 1032) where two fluorescent labels contribute to a measured signal and in FIG. 1B (1041 and 1042) where a single fluorescent label contributes to a measured signal. Intensity values represented by solid lines, e.g. 1033, are from label "a," and intensity values represented by dashed lines, e.g. 1036, are from label "b". The presence of solid and dashed lines in both channels of FIG. 1A reflects overlapping emission bands of the fluorescent labels, which when collected together complicates analysis because amounts of a measured intensity are from both labels. In FIG. 1B, where only a single fluorescent label contributes to the measured signal, intensity values do not contain contributions due to overlapping emission bands of other labels, thereby making label (and therefore nucleotide) determination easier.

Controlling Translocation Speed

The role of translocation speed of polynucleotides through nanopores and the need for its control have been appreciated in the field of nanopore technology wherein changes in electric current are use to identify translocating analytes. A wide variety of methods have been used to control translocation speed, which include both methods that can be adjusted in real-time without significant difficulty (e.g. voltage potential across nanopores, temperature, and the like) and methods that can be adjusted during operation only with difficulty (reaction buffer viscosity, presence or absence of charged side chains in the bore of a protein nanopore, ionic composition and concentration of the reaction buffer, velocity-retarding groups attached or hybridized to polynucleotide analytes, molecular motors, and the like), e.g. Bates et al, Biophysical J., 84: 2366-2372 (2003); Carson et al, Nanotechnology, 26(7): 074004 (2015); Yeh et al, Electrophoresis, 33(23): 58-65 (2012); Meller, J. Phys. Cond. Matter, 15: R581-R607 (2003); Luan et al, Nanoscale, 4(4): 1068-1077 (2012); Keyser, J. R. Soc. Interface, 8: 1369-1378 (2011); and the like, which are incorporated herein by reference. In some embodiments, a step or steps are included for active control of translocation speed while a method of the invention is being implemented, e.g. voltage potential, temperature, or the like; in other embodiments, a step or steps are included that determine a translocation speed that is not actively controlled or changed while a method of the invention is being implemented, e.g. reaction buffer viscosity, ionic concentration, and the like. In regard to the latter, in some embodiments, a translocation speed is selected by providing a reaction buffer having a concentration of glycerol, or equivalent reagent, in the range of from 1 to 60 percent.

In regard to the former embodiments (with real-time translocation speed adjustment), a measure of whether one or more than one label is contributing fluorescence to measured signals may be based on the distribution of fluorescence intensity among a plurality of channels over which fluorescence is collected. Typically the plurality of channels typically include 2, 3, or 4 channels corresponding to the emission bands of the fluorescent labels used, e.g. to label different kinds of nucleotide. In a measured sample of fluorescence emanating from a region adjacent to a nanopore exit, if only a single label contributes to a measured signal, the relative distribution of signal intensity among the different channels (e.g. 4 channels) could be represented ideally as (1,0,0,0); (0,1,0,0); (0,0,1,0) or (0,0,0,1). On the other hand, if more than one label contributed to a measured fluorescent signal, the relative distributions would include non-zero values in more than one channel, with a worse case being four different labels contributing equally, which would appear as (0.25,0.25,0.25,0.25) in the above representation. A measure which would vary monotonically between a maximum value corresponding to relative intensity distributions (1,0,0,0); (0,1,0,0); (0,0,1,0) or (0,0,0,1) and a minimum value corresponding to a relative intensity distribution of (0.25,0.25,0.25,0.25) may be used for controlling in real-time a translocation speed. For example, an initial translocation speed could be lowered based on the value of such a measure that was near its minimum. Such lowering may be implemented, for example, by lowering a potential voltage across the nanopores by a predetermined amount, after which the measure could be re-calculated. Such steps could be repeated until the process was optimized, e.g. to maximize the fraction of measurements wherein collected signals emanate from only a single label.

As mentioned above, translocation speeds depend in part on the voltage difference (or electrical field strength) across a nanopore and conditions in the reaction mixture, or buffer, of a first chamber where polynucleotides are exposed to the nanopores (e.g. disposed in a solid phase membrane making up one wall of the first chamber). Polynucleotide capture rates by nanopores depend on concentration of such polynucleotides. In some embodiments, conventional reaction mixture conditions for nanopore sequencing may be employed with the invention (for controlling translocation speed by varying voltage potential across nanopores), for example, 1M KCl (or equivalent salt, such as NaCl, LiCl, or the like) and a pH buffering system (which, for example, ensures that proteins being used, e.g. protein nanopores, nucleases, or the like, are not denatured). In some embodiments, a pH buffering system may be used to keep the pH substantially constant at a value in the range of 6.8 to 8.8. In some embodiments, a voltage difference across the nanopores may be in the range of from 70 to 200 mV. In other embodiments, a voltage difference across the nanopores may be in the range of from 80 to 150 mV. An appropriate voltage for operation may be selected using conventional measurement techniques. Current (or voltage) across a nanopore may readily be measured using commercially available instruments. A voltage difference may be selected so that translocation speed is within a desired range. In some embodiments, a range of translocation speeds comprises those speeds less than 1000 nucleotides per second. In other embodiments, a range of translocation speeds is from 10 to 800 nucleotides per second; in other embodiments, a range of translocation speeds is from 10 to 600 nucleotides per second; in other embodiments, a range of translocation speeds is from 200 to 800 nucleotides per second; in other embodiments, a range of translocation speeds is from 200 to 500 nucleotides per second. Likewise, other factors affecting translocation speed, e.g. temperature, viscosity, ion concentration, charged side chains in the bore of a protein nanopore, and the like, may be selected to obtain translocation speeds in the ranges cited above.

In some embodiments, a device for implementing the above methods for single stranded nucleic acids typically includes providing a set of electrodes for establishing an electric field across the nanopores (which may comprise an array). Single stranded nucleic acids are exposed to nanopores by placing them in an electrolyte (i.e. reaction buffer) in a first chamber, which is configured as the "cis" side of the layered membrane by placement of a negative electrode in the chamber. Upon application of an electric field, the negatively single stranded nucleic acids are captured by nanopores and translocated to a second chamber on the other side of the layered membrane, which is configured as the "trans" side of membrane by placement of a positive electrode in the chamber. As mentioned above, the speed of translocation depends in part on the ionic strength of the electrolytes in the first and second chambers and the applied voltage across the nanopores. In optically based detection, a translocation speed may be selected by preliminary calibration measurements, for example, using predetermined standards of labeled single stranded nucleic acids that generate signals at different expected rates per nanopore for different voltages. Thus, for DNA sequencing applications, an initial translocation speed may be selected based on the signal rates from such calibration measurements, as well as the measure based on relative signal intensity distribution discussed above. Consequently, from such measurements a voltage may be selected that permits, or maximizes, reliable nucleotide identifications, for example, over an array of nanopores. In some embodiments, such calibrations may be made using nucleic acids from the sample of templates being analyzed (instead of, or in addition to, predetermined standard sequences). In some embodiments, such calibrations may be carried out in real time during a sequencing run and the applied voltage may be modified in real time based on such measurements, for example, to maximize the acquisition of nucleotide-specific signals.

Embodiments Employing Mutually and Self-Quenching Labels

As mentioned above, in some embodiments, self- and mutually quenching fluorescent labels may be used in addition to quenching agents in order to reduce fluorescent emissions outside of those from labels on nucleotides exiting nanopores. Use of such fluorescent labels is disclosed in U.S. patent publication 2016/0122812, which is incorporated by reference. In some embodiments, monomers are labeled with fluorescent labels that are capable of at least three states while attached to a target polynucleotide: (i) A substantially quenched state wherein fluorescence of an attached fluorescent label is quenched by a fluorescent label on an immediately adjacent monomer; for example, a fluorescent label attached to a polynucleotide in accordance with the invention is substantially quenched when the labeled polynucleotide is free in conventional aqueous solution for studying and manipulating the polynucleotide. (ii) A sterically constrained state wherein a labeled polynucleotide is translocating through a nanopore such that the free-solution movements or alignments of an attached fluorescent label is disrupted or limited so that there is little or no detectable fluorescent signal generated from the fluorescent label. (iii) A transition state wherein a fluorescent label attached to a polynucleotide transitions from the sterically constrained state to the quenched state as the fluorescent label exits the nanopore (during a "transition interval") while the polynucleotide translocates through the nanopore.

In part, this example is an application of the discovery that during the transition interval a fluorescent label (on an otherwise substantially fully labeled and self-quenched polynucleotide) is capable of generating a detectable fluorescent signal. Without the intention of being limited by any theory underlying this discovery, it is believed that the fluorescent signal generated during the transition interval is due to the presence of a freely rotatable dipole in the fluorescent label emerging from the nanopore, which renders the fluorescent label temporarily capable of generating a fluorescent signal, for example, after direct excitation or via FRET. In both the sterically constrained state as well as the quenched state, the dipoles are limited in their rotational freedom thereby reducing or limiting the number of emitted photons. In some embodiments, the polynucleotide is a polynucleotide, usually a single stranded polynucleotide, such as, DNA or RNA, but especially single stranded DNA. In some embodiments, the invention includes a method for determining a nucleotide sequence of a polynucleotide by recording signals generated by attached fluorescent labels as they exit a nanopore one at a time as a polynucleotide translocates through the nanopore. Upon exit, each attached fluorescent label transitions during a transition interval from a constrained state in the nanopore to a quenched state on the polynucleotide in free solution. In other words, in some embodiments, a step of the method of the invention comprises exciting each fluorescent label as it is transitioning from a constrained state in the nanopore to a quenched state on the polynucleotide in free solution. As mentioned above, during this transition interval or period the fluorescent label is capable of emitting a detectable fluorescent signal indicative of the nucleotide it is attached to.

In some embodiments, the invention includes an application of the discovery that fluorescent labels and nanopores may be selected so that during translocation of a polynucleotide through a nanopore fluorescent labels attached to monomers are forced into a constrained state in which they are incapable (or substantially incapable) of producing a detectable fluorescent signal. In some embodiments, nanopores are selected that have a bore, or lumen, with a diameter in the range of from 1 to 4 nm; in other embodiments, nanopores are selected that have a bore or lumen with a diameter in the range of from 2 to 3 nm. In some embodiments, such bore diameters are provided by a protein nanopore. In some embodiments, such nanopores are used to force fluorescent labels into a constrained state in accordance with the invention, so that whenever a fluorescent label exits a nanopore, it transitions from being substantially incapable of generating a fluorescent signal to being detectable and identifiable by a fluorescent signal it can be induced to emit. Thus, fluorescent labels attached to each of a sequence of monomers of a polynucleotide may be detected in sequence as they suddenly generate a fluorescent signal in a region immediately adjacent to a nanopore exit (a "transition zone" or "transition volume" or "detection zone"). In some embodiments, organic fluorescent dyes are used as fluorescent labels with nanopores of the above diameters. In some embodiments, at least one such organic fluorescent dye is selected from the set consisting of xanthene dyes, rhodamine dyes and cyanine dyes. Some embodiments for determining a monomer sequence of a polynucleotide may be carried out with the following steps: (a) translocating a polynucleotide through a nanopore, wherein monomers of the polynucleotide are labeled with fluorescent labels wherein the nanopore constrains fluorescent labels within its bore into a constrained state such that substantially no detectable fluorescent signal is generated therein; (b) exciting the fluorescent label of each monomer upon exiting the nanopore; (c) measuring a fluorescent signal in a detection zone generated by the exiting fluorescent label to identify the monomer to which the fluorescent label is attached; (d) quenching fluorescent signals from excited fluorescent labels outside of the detection zone, and (d) determining a monomer sequence of the polynucleotide from a sequence of fluorescent signals. In further embodiments, fluorescent labels are acceptors of a FRET pair and one or more donors of the FRET pair are attached to the nanopore within a FRET distance of the exit.

In some embodiments, "substantially quenched" as used above means a fluorescent label generates a fluorescent signal at least thirty percent reduced from a signal generated under the same conditions, but without adjacent mutually quenching labels. In some embodiments, "substantially quenched" as used above means a fluorescent label generates a fluorescent signal at least fifty percent reduced from a signal generated under the same conditions, but without adjacent mutually quenching labels.

In some embodiments, a nucleotide sequence of a target polynucleotide is determined by carrying out four separate reactions in which copies of the target polynucleotide have each of its four different kinds of nucleotide (A, C, G and T) labeled with a single fluorescent label. In a variant of such embodiments, a nucleotide sequence of a target polynucleotide is determined by carrying out four separate reactions in which copies of the target polynucleotide have each of its four different kinds of nucleotide (A. C, G and T) labeled with one fluorescent label while at the same time the other nucleotides on the same target polynucleotide are labeled with a second fluorescent label. For example, if a first fluorescent label is attached to A's of the target polynucleotide in a first reaction, then a second fluorescent label is attached to C's, G's and T's (i.e. to the "not-A" nucleotides) of the target polynucleotides in the first reaction. Likewise, in continuance of the example, in a second reaction, the first label is attached to C's of the target polynucleotide and the second fluorescent label is attached to A's, G's and T's (i.e. to the "not-C" nucleotides) of the target polynucleotide. And so on, for nucleotides G and T.

The same labeling scheme may be expressed in terms of conventional terminology for subsets of nucleotide types; thus, in the above example, in a first reaction, a first fluorescent label is attached to A's and a second fluorescent label is attached to B's; in a second reaction, a first fluorescent label is attached to C's and a second fluorescent label is attached to D's; in a third reaction, a first fluorescent label is attached to G's and a second fluorescent label is attached to H's; and in a fourth reaction, a first fluorescent label is attached to T's and a second fluorescent label is attached to V's.

In some embodiments, a polymer, such as a polynucleotide or peptide, may be labeled with a single fluorescent label attached to a single kind of monomer, for example, every T (or substantially every T) of a polynucleotide is labeled with a fluorescent label, e.g. a cyanine dye. In such embodiments, a collection, or sequence, of fluorescent signals from the polynucleotide may form a signature or fingerprint for the particular polynucleotide. In some such embodiments, such fingerprints may or may not provide enough information for a sequence of monomers to be determined.

In some embodiments, a feature of the invention is the labeling of substantially all monomers of a polynucleotide analyte with fluorescent dyes or labels that are members of a mutually quenching set. The use of the term "substantially all" in reference to labeling polynucleotide analytes is to acknowledge that chemical and enzymatic labeling techniques are typically less than 100 percent efficient. In some embodiments, "substantially all" means at least 80 percent of all monomer have fluorescent labels attached. In other embodiments, "substantially all" means at least 90 percent of all monomer have fluorescent labels attached. In other embodiments, "substantially all" means at least 95 percent of all monomer have fluorescent labels attached. Mutually quenching sets of fluorescent dyes have the following properties: (i) each member quenches fluorescence of every member (for example, by FRET or by static or contact mechanisms), and (ii) each member generates a distinct fluorescent signal when excited and when in a non-quenched state. That is, if a mutually quenching set consists of two dyes, D1 and D2, then (i) D1 is self-quenched (e.g. by contact quenching with another D1 molecule) and it is quenched by D2 (e.g. by contact quenching) and (ii) D2 is self-quenched (e.g. by contact quenching with another D2 molecule) and it is quenched by D1 (e.g. by contact quenching). Guidance for selecting fluorescent dyes or labels for mutually quenching sets may be found in the following references, which are incorporated herein by reference: Johansson, Methods in Molecular Biology, 335: 17-29 (2006); Marras et al, Nucleic Acids Research, 30: e122 (2002); and the like. In some embodiments, members of a mutually quenching set comprise organic fluorescent dyes that components or moieties capable of stacking interactions, such as aromatic ring structures. Exemplary mutually quenching sets of fluorescent dyes, or labels, may be selected from rhodamine dyes, fluorescein dyes and cyanine dyes. In one embodiment, a mutually quenching set may comprise the rhodamine dye, TAMRA, and the fluorescein dye, FAM. In another embodiment, mutually quenching sets of fluorescent dyes may be formed by selecting two or more dyes from the group consisting of Oregon Green 488, Fluorescein-EX, fluorescein isothiocyanate, Rhodamine Red-X, Lissamine rhodamine B, Calcein, Fluorescein, Rhodamine, one or more BODIPY dyes, Texas Red, Oregon Green 514, and one or more Alexa Fluors. Representative BODIPY dyes include BODIPY FL, BODIPY R6G, BODIPY TMR, BODIPY 581/591, BODIPY TR, BODIPY 630/650 and BODIPY 650/665. Representative Alexa Fluors include Alexa Fluor 350, 405, 430, 488, 500, 514, 532, 546, 555, 568, 594, 610, 633, 647, 660, 680, 700, 750 and 790.

As above, in some embodiments, a monomer sequence of a target polynucleotide is determined by carrying out separate reactions (one for each kind of monomer) in which copies of the target polynucleotide have each different kind of monomer labeled with a mutually- or self-quenching fluorescent label. In other embodiments, a monomer sequence of a target polynucleotide is determined by carrying out separate reactions (one for each kind of monomer) in which copies of the target polynucleotide have each different kind of monomer labeled with a different mutually quenching fluorescent label selected from the same mutually quenching set. In embodiments in which a mutually quenching set contains only two dyes, then a selected monomer (say, monomer X) is labeled with a first mutually quenching dye and every other kind of monomer (i.e., not-monomer X) is labeled with a second mutually quenching dye from the same set. Thus, steps of the embodiment generate a sequence of two different fluorescent signals, one indicating monomer X and another indicating not-monomer X.

In some embodiments, a single fluorescent label (for example, attached to a single kind of monomer in a polynucleotide comprising multiple kinds of monomers) may be used that is self-quenching when attached to adjacent monomers (of the same kind) on a polynucleotide, such as adjacent nucleotides of a polynucleotide. Exemplary self-quenching fluorescent labels include, but are not limited to, Oregon Green 488, fluorescein-EX, FITC, Rhodamine Red-X, Lissamine rhodamine B, calcein, fluorescein, rhodamine, BODIPYS, and Texas Red, e.g. which are disclosed in Molecular Probes Handbook, 11th Edition (2010).

Embodiments Employing Quenching Agents

Figure 2A:
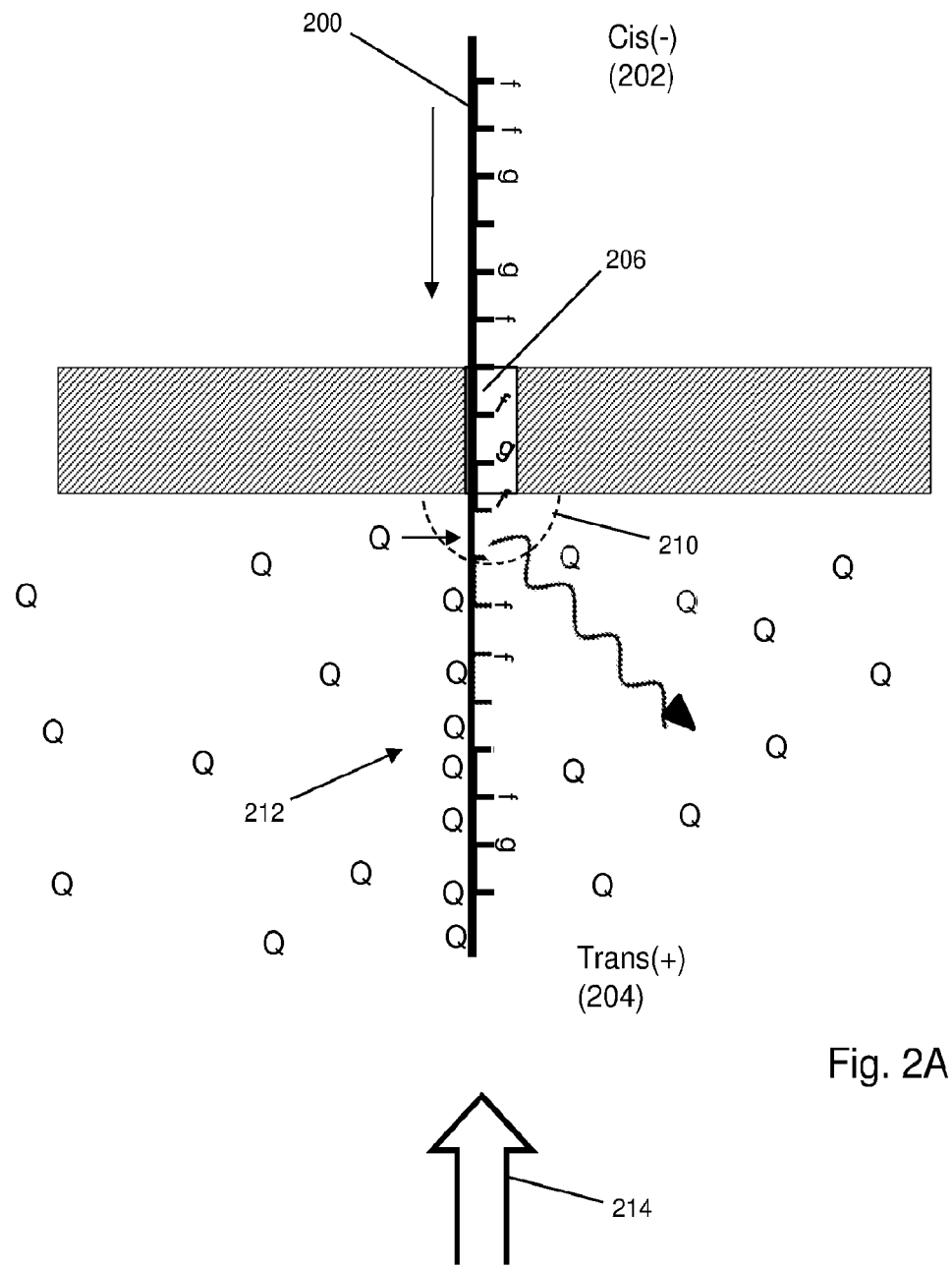
FIGS. 2A-2C illustrate embodiments of the invention employing quenching agents in a trans chamber, a cis chamber and in both cis and trans chambers.
Figure 2B:
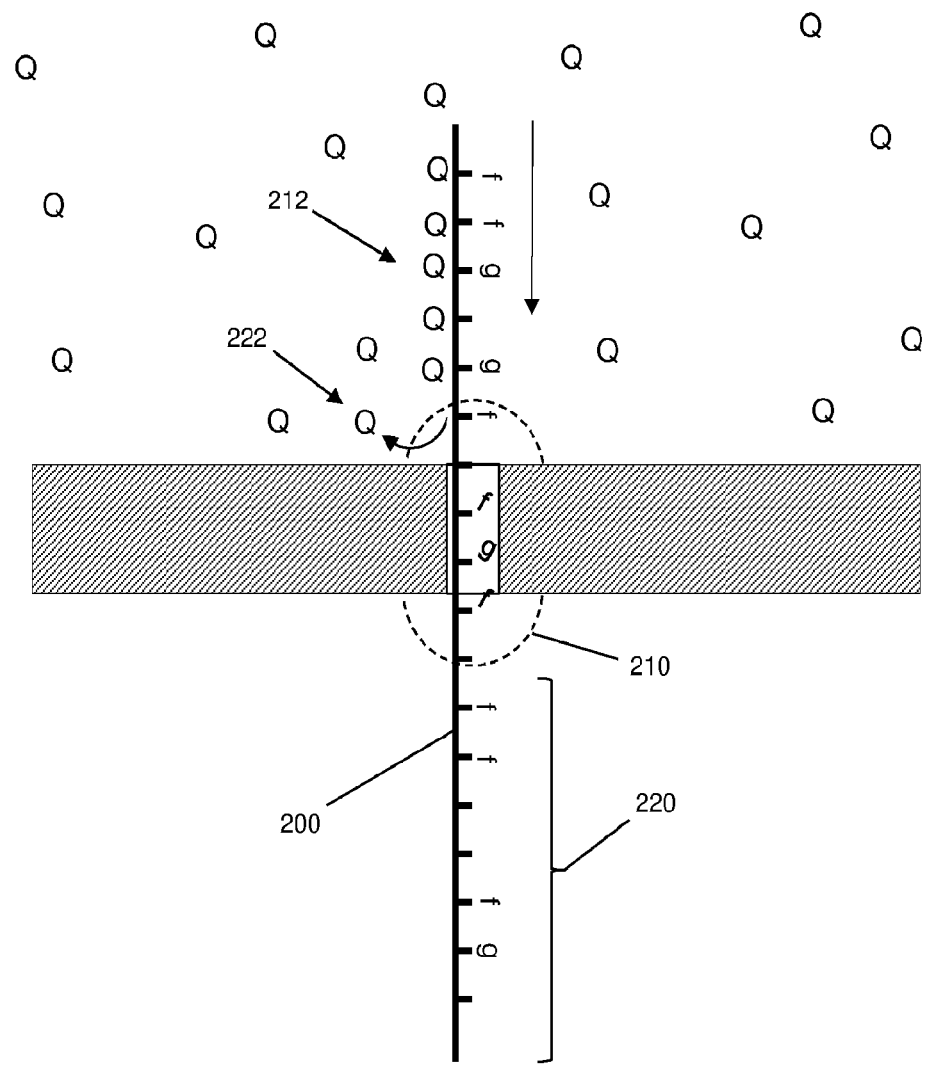
Figure 2C:
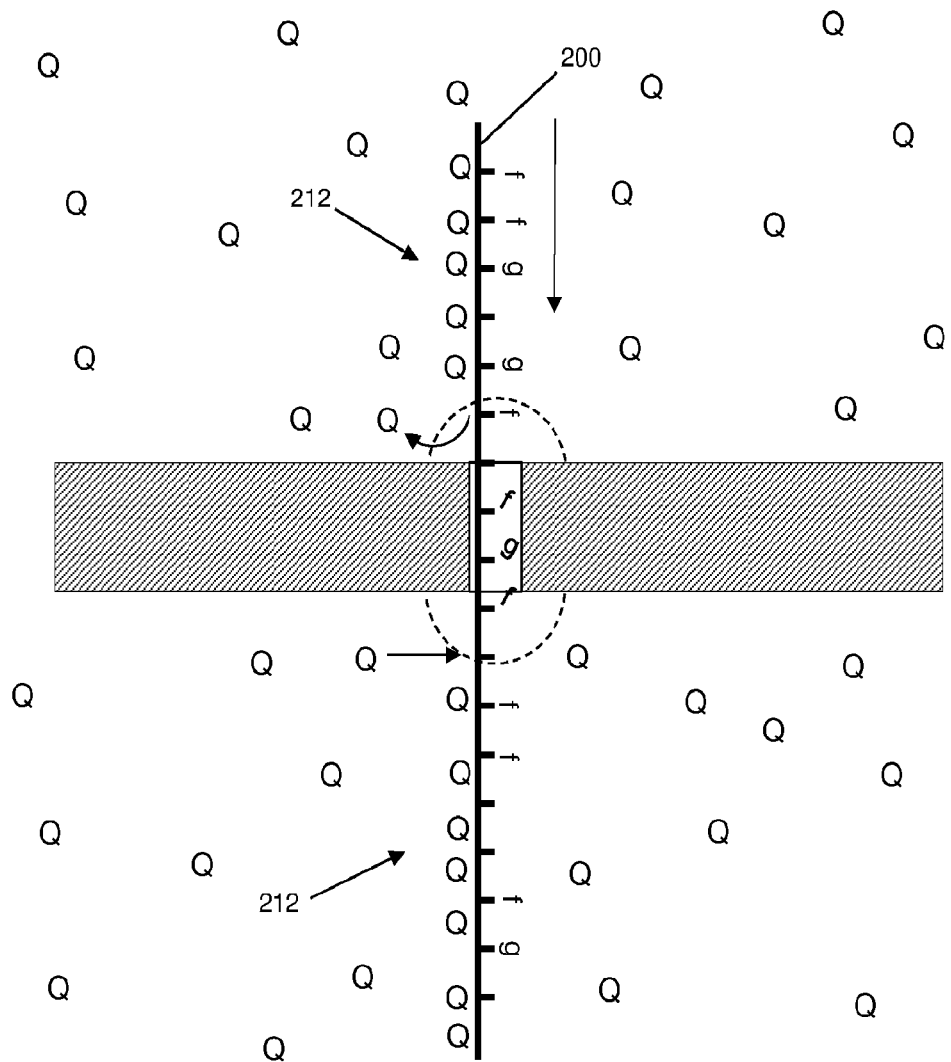

FIGS. 2A-2C illustrate different embodiments of the invention corresponding to where quenching agents are applied in a nanopore device: trans chamber only (FIG. 2A), cis chamber only (FIG. 2B), or both cis and trans chambers (FIG. 2C). In FIG. 2A, labeled polynucleotide (200) is illustrated translocating nanopore (206) of solid phase membrane (208) from cis chamber (202) to trans chamber (204). Immersed in trans chamber (204) are non-fluorescent quenching agents (205) designated by "Q". Quenching agents of the invention are soluble under translocation conditions for labeled polynucleotide (200), and under the same conditions, quenching agents bind to single stranded polynucleotides, such as (200), without substantial sequence specificity. As explained more fully below, a large variety of non-fluorescent quenching agents are available for use with the invention, which include derivatives of many well-known organic dyes, such as asymmetric cyanine dyes, as well as conjugates of such compounds and oligonucleotides and/or analogs thereof. In this embodiment, selection of the type and concentration of quenching agent and the translocation speed define detection zone (210). In some embodiments, "detection zone" means a region or volume (which may be contiguous or non-contiguous) from which fluorescent signals are collected to form the raw data from which information, such as sequence information, about a labeled polynucleotide is determined. Fluorescent labels in trans chamber (204) outside of detection zone (210) are substantially quenched by quenching agents (205) bound to the portion of labeled polynucleotide (200) in trans chamber (204). In some embodiments, quenching agents comprise an oligonucleotide or analog conjugated to one or more quenching moieties based on organic dyes as described more fully below. Embodiments of FIG. 2A may be employed when, for example, solid phase membrane (208) is or comprises an opaque layer so that fluorescent labels in cis chamber (202) are substantially non-excited.

FIG. 2B shows substantially the same elements as those in FIG. 2A with the exception that quenching agents (205) are disposed in cis chamber (202). This configuration may be desirable under circumstances where undesired evanescent waves, or like non-radiative light energy, extend to cis chamber (202) and excite fluorescent labels which generate fluorescent signals that are collected. Quenching agents (205) that bind to labeled polynucleotide (200) in cis chamber (202) reduce or eliminate such fluorescent signals. In some embodiments, quenching agents (205) and cross-section of nanopore (206) are selected so that quenching agents (205) are excluded from translocating through nanopore (206). In some embodiments, this may be achieved by using protein nanopore α-hemolysin and quenching agents comprising conjugates of oligonucleotides or analogs thereof and one or more quenching compounds, as described more fully below.

FIG. 2C illustrates an embodiment where quenching agents (205) are present in both cis chamber (202) and trans chamber (204), which provides the advantages described for the embodiments of both FIGS. 2A and 2B.

Figure 3:
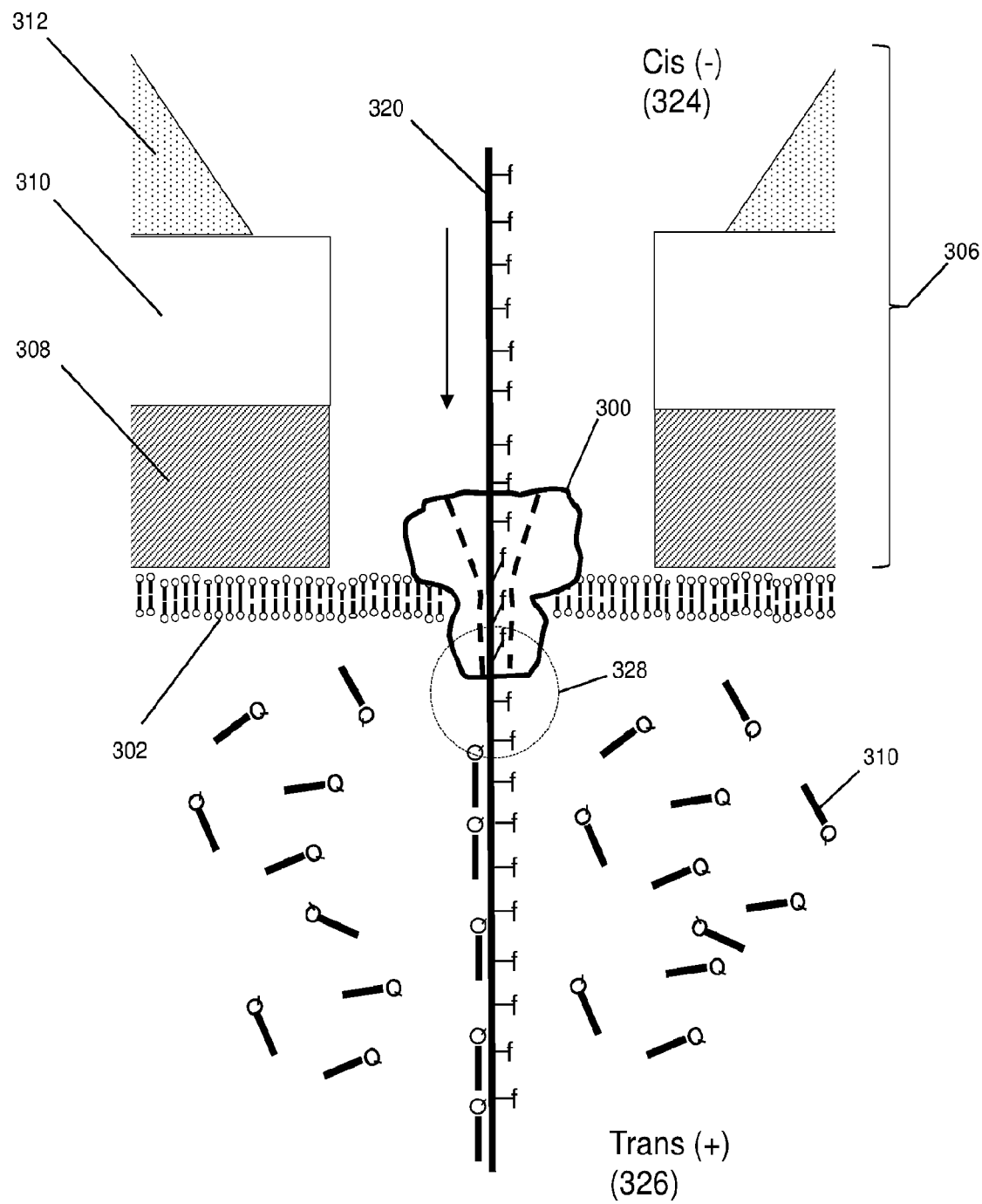
FIG. 3 illustrates an embodiment of the invention using a protein nanopore and epi-illumination with a metal layer on the nanopore array to reduce background or TIR with FRET excitation.

FIG. 3 illustrates an embodiment which includes the following elements: protein nanopore (300) disposed in lipid bilayer (302); epi-illumination of fluorescent labels with opaque layer (308) in solid phase membrane (306) to prevent or reduce background fluorescence; and quenching agents (310) disposed in trans chamber (326). As above, polynucleotide (320) with fluorescently labeled nucleotides (labels being indicated by "f", as with (322)) is translocated through nanopore (300) from cis chamber (324) to trans chamber (326). Oligonucleotide quenchers (310) are disposed in trans chamber (326) under conditions (e.g. concentration, temperature, salt concentration, and the like) that permits hybridization of oligonucleotide quenchers (328) to portions of polynucleotide (320) emerging from nanopore (300). Nanopore (300) may be selected so that signals from fluorescent labels are suppressed during transit of the nanopore as described in Huber et al, U.S. patent publication US 2016/0076091, which is incorporated herein by reference. Thus, when labeled nucleotides emerge from nanopore (300) in region (328) they become unsuppressed and capable of generating a signal. With most if not all forms of direct illumination (e.g. non-FRET) such emerged labels would continue to emit fluorescence as they travel further into trans chamber (326), thereby contributing greatly to a collected signal. With quenching agents in trans chamber (326) that bind to the emerging polynucleotide, such emissions can be significantly reduced and can define detection zone (328) from which collected signals can be analyzed to give nucleotide sequence information about polynucleotide (320). In some embodiments, a fluorescent signal from a single fluorescent label is detected from detection zone (328) during a detection period as the labeled polynucleotide moves through the detection zone. In other embodiments, a plurality of fluorescent signals is collected from a plurality of fluorescent labels in detection zone (328) during a predetermined time period. In some embodiments, such detection period is less than 1 msec, or less than 0.1 msec, or less than 0.01 msec. In some embodiments, such detection period is at least 0.01 msec, or at least 0.1 msec, or at least 0.5 msec.

Quenching agents of the invention comprise any compound (or set of compounds) that under nanopore sequencing conditions is (i) substantially non-fluorescent, (ii) binds to single stranded nucleic acids, particularly single stranded DNA, and (iii) absorbs excitation energy from other molecules non-radiatively and releases it non-radiatively. In some embodiments, quenching agents further bind non-covalently to single stranded DNA. A large variety of quenching compounds are available for use with the invention including, but not limited to, non-fluorescent derivatives of common synthetic dyes such as cyanine and xanthene dyes, as described more fully below. Guidance in selecting quenching compounds may be found in U.S. Pat. Nos. 6,323,337; 6,750,024 and like references, which are incorporated herein by reference.

In some embodiments, a quenching agent may be a single stranded DNA binding dye that has been covalently modified with a heavy atom that is known to quench fluorescence (such as bromine or iodine), or covalently modified with other groups known to quench fluorescence, such as a nitro group or a azo group. An example of dye that is known to bind single stranded DNA is Sybr Green (Zipper et al, (2004), Nucleic Acids Research. 32 (12)). Incorporation of a nitro, bromine, iodine, and/or azo groups into the cyanine Sybr Green structure provides a single stranded DNA binding group moiety that will quench fluorescent labels that might be present on a DNA.

In some embodiments, quenching agents comprise a binding moiety and one or more quenching moieties. Binding moieties may include any compound that binds to single stranded nucleic acids without substantial sequence specificity. Binding moieties may comprise peptides or oligonucleotides or analogs of either having modified linkages and/or monomers. Oligonucleotides and their analogs may provide binding to polynucleotides via duplex formation or via non-base paired aptameric binding. In some embodiments, binding moieties comprise an oligonucleotide or analog thereof having a length in the range of from 6 to 60 nucleotides. Such oligonucleotides or analogs may be conjugated to one quenching moiety or to a plurality of quenching moieties. In some embodiments, the plurality of quenching moieties conjugated to each oligonucleotide or analog is 2 or 3. Quenching moieties conjugated to a binding moiety may be the same or different. In some embodiments, whenever a binding moiety is an oligonucleotide or analog, two quenching moieties are conjugated thereto, one at a 5' end and one at a 3' end of the oligonucleotide. Oligonucleotides or analogs having from 2 to 3 quenching moieties may be synthesized using conventional linkage and synthetic chemistries, for example, as disclosed in the references cited herein.

Oligonucleotides or analogs may be provided as a single species or they may be provided as mixtures of a plurality of oligonucleotides or analogs with different sequences, and therefore, different binding specificities. In some embodiments, oligonucleotides or analogs are random sequence polymers; that is, they are provided as mixtures of every possible sequence of a given length. For example, such oligonucleotides or analogs may be represented by the formulas, "NNNNNN" for 6-mers, or "NNNNNNNN" for 8-mers, wherein N may be A, C, G or T, or an analog thereof.

"Analogs" in reference to oligonucleotides means an oligonucleotide that contains one or more nucleotide analogs. As described in the definition section, a "nucleotide analog" is a nucleotide that may have a modified linkage moiety, sugar moiety or base moiety. Exemplary oligonucleotide analogs that may be used with the invention include, but are not limited to, peptide nucleic acids (PNAs), locked nucleic acids (LNAs)(2'-O-methyl RNA), phosphorothioate oligonucleotides, bridged nucleic acids (BNAs), or the like.

In some embodiments, oligonucleotide binding moieties comprise universal bases; that is, they contain one or more nucleotide analogs that can replace any of the four natural nucleotides without destabilizing base-pair interactions. Nucleotide analogs having universal base properties are described in Loakes, Nucleic Acids Research, 29(12): 2437-2447 (2001), which is incorporated herein by reference. In some embodiments, oligonucleotide binding moieties comprise 2'-deoxyinosine, 7-deaza-2'-deoxyinosine, 2-aza-2'-deoxyinosine, 3-nitropyrrole nucleotides, 5-nitroindole nucleotides, or the like.

In some embodiments, quenching agents may comprise a combination of two or more compounds that act together to quench undesired fluorescent signals of a single stranded labeled polynucleotide. For example, a quenching agent may comprise an oligonucleotide (e.g., polydeoxyinosine) that may form a duplex with the labeled polynucleotide and separately a double stranded intercalator that is a quencher. Thus, whenever the polydeoxyinosine binds to a labeled polynucleotide, the quenching intercalator binds to the resulting duplex and quenches fluorescent signals from the polynucleotide.

Any synthetic dye that can detectably quench fluorescent signals of the fluorescent labels of a labeled polynucleotide is an acceptable quenching moiety for the purposes of the invention. Specifically, as used in the invention, the quenching moieties possess an absorption band that exhibits at least some spectral overlap with an emission band of the fluorescent labels on a labeled polynucleotide. This overlap may occur with emission of the fluorescent label (donor) occurring at a lower or even higher wavelength emission maximum than the maximal absorbance wavelength of the quenching moiety (acceptor), provided that sufficient spectral overlap exists. Energy transfer may also occur through transfer of emission of the donor to higher electronic states of the acceptor. One of ordinary skill in the art determines the utility of a given quenching moiety by examination of that dye's excitation bands with respect to the emission spectrum of the fluorescent labels being used.

Typically, fluorescence quenching in the invention occurs through Fluorescence Resonance Energy Transfer (FRET or through the formation of charge transfer complexes) between a fluorescent label and a quenching moiety of the invention. The spectral and electronic properties of the donor and acceptor compounds have a strong effect on the degree of energy transfer observed, as does the separation distance between the fluorescent labels on the labeled polynucleotide and the quenching moiety. As the separation distance increases, the degree of fluorescence quenching decreases.

A quenching moiety may be optionally fluorescent, provided that the maximal emission wavelength of the dye is well separated from the maximal emission wavelength of the fluorescent labels when bound to labeled polynucleotides. Preferably, however, the quenching moiety is only dimly fluorescent, or is substantially non-fluorescent, when covalently conjugated to a oligonucleotide or analog. Substantially non-fluorescent, as used herein, indicates that the fluorescence efficiency of the quenching moiety in an assay solution as described for any of the methods herein is less than or equal to 5 percent, preferably less than or equal to 1 percent. In other embodiments, the covalently bound quenching moiety exhibits a quantum yield of less than about 0.1, more preferably less than about 0.01. In some embodiments, the fluorescence of fluorescent labels associated with a quenching oligonucleotide of the invention is quenched more than 50% relative to the same oligonucleotide associated with the same fluorescent labels in the absence of the covalently bound quenching moiety. In another embodiment, the fluorescent labels are quenched more than 90% relative to the unlabeled oligonucleotide. In yet another embodiment, the nucleic acid stains are quenched more than 95% relative to the unlabeled oligonucleotide.

In some embodiments, a quenching moiety may be a pyrene, an anthracene, a naphthalene, an acridine, a stilbene, an indole or benzoindole, an oxazole or benzoxazole, a thiazole or benzothiazole, a 4-amino-7-nitrobenz-2-oxa-1,3-diazole (NBD), a cyanine, a carbocyanine, a carbostyryl, a porphyrin, a salicylate, an anthranilate, an azulene, a perylene, a pyridine, a quinoline, a coumarin (including hydroxycoumarins and aminocoumarins and fluorinated and sulfonated derivatives thereof (as described in U.S. Pat. No. 5,830,912 to Gee et al. (1998) and U.S. Pat. No. 5,696,157 to Wang et al. (1997), incorporated by reference), a polyazaindacene (e.g. U.S. Pat. No. 4,774,339 to Haugland, et al. (1988); U.S. Pat. No. 5,187,288 to Kang, et al. (1993); U.S. Pat. No. 5,248,782 to Haugland, et al. (1993); U.S. Pat. No. 5,274,113 to Kang, et al. (1993); U.S. Pat. No. 5,433,896 to Kang, et al. (1995); U.S. Pat. No. 6,005,113 to Wu et al. (1999), all incorporated by reference), a xanthene, an oxazine or a benzoxazine, a carbazine (U.S. Pat. No. 4,810,636 to Corey (1989), incorporated by reference), or a phenalenone or benzphenalenone (U.S. Pat. No. 4,812,409 Babb et al. (1989), incorporated by reference).

In other embodiments, quenching moieties that are substantially non-fluorescent dyes include in particular azo dyes (such as DABCYL or DABSYL dyes and their structural analogs), triarylmethane dyes such as malachite green or phenol red, 4',5z-diether substituted fluoresceins (U.S. Pat. No. 4,318,846 (1982)), or asymmetric cyanine dye quenchers (PCT Int. App. WO 99 37,717 (1999)).

In embodiments where the quenching moiety is a xanthene, the synthetic dye is optionally a fluorescein, a rhodol (U.S. Pat. No. 5,227,487 to Haugland, et al. (1993), incorporated by reference), or a rhodamine. As used herein, fluorescein includes benzo- or dibenzofluoresceins, seminaphthofluoresceins, or naphthofluoresceins. Similarly, as used herein rhodol includes seminaphthorhodafluors (U.S. Pat. No. 4,945,171 to Haugland, et al. (1990), incorporated by reference). Xanthenes include fluorinated derivatives of xanthene dyes (Int. Publ. No. WO 97/39064, Molecular Probes, Inc. (1997), incorporated by reference), and sulfonated derivatives of xanthene dyes (Int. Publ. No. WO 99/15517, Molecular Probes, Inc. (1999), incorporated by reference). As used herein, oxazines include resorufms, aminooxazinones, diaminooxazines, and their benzo-substituted analogs.

In further embodiments, the quenching moiety is an substantially nonfluorescent derivative of 3- and/or 6-amino xanthene that is substituted at one or more amino nitrogen atoms by an aromatic or heteroaromatic ring system, e.g. as described in U.S. Pat. No. 6,399,392, which is incorporated herein by reference. These quenching dyes typically have absorption maxima above 530 nm, have little or no observable fluorescence and efficiently quench a broad spectrum of luminescent emission, such as is emitted by chemiluminiphores, phosphors, or fluorophores. In one embodiment, the quenching dye is a substituted rhodamine. In another embodiment, the quenching compound is a substituted rhodol.

In still other embodiments, a quenching moiety may comprise one or more non-fluorescent quenchers known as Black Hole Quenchers™ compounds (BHQs) described in the following patents, which are incorporated herein by reference: U.S. Pat. Nos. 7,019,129; 7,109,312; 7,582,432; 8,410,025; 8,440,399; 8,633,307; 8,946,404; 9,018,369; or 9,139,610.

Additional quenching moieties are disclosed in the following, which are incorporated herein by reference: U.S. Pat. Nos. 6,699,975; 6,790,945; and 8,114,979.

Embodiments Employing Two or Three Optical Labels

In some embodiments, as few as two different kinds of nucleotide are labeled with different optical labels that generate distinguishable optical signals for the selected kinds of nucleotide in both sense strands and antisense strands of target polynucleotides. For example, C's and T's of the complementary strands of each target polynucleotide may be replaced by labeled analogs, wherein the labels of the C and T analogs are capable of generating distinct optical signals. Optical signatures are then generated by translocating the labeled strands through nanopores where nucleotides of the strands are constrained to pass sequentially through an optical detection region where their labels are caused to generate optical signals. In some embodiments, information from optical signatures from both sense and antisense strands are combined to determine a nucleotide sequence of target polynucleotides.

In some embodiments, the selected kinds of nucleotides of target polynucleotides are replaced by labeled nucleotide analogs in an extension reaction using a nucleic acid polymerase. Labeled strands of target polynucleotides are translocated through nanopores that constrain the nucleotides of strands to move single file through an optical detection region where they are excited so that they produce an optical signal. A collection of optical signals for an individual strand is referred to herein as an optical signature of the strand. In some embodiments, where a strand and its complement (i.e. sense and antisense strands) are linked, for example, via a hairpin adaptor, a single optical signature may include optical signals from optical labels on nucleotides from both the sense strand and the antisense strand. In other embodiments, different strands of a target polynucleotide may separately generate two different optical signatures which may be combined, or used together, for analysis, as mentioned above. Such separately analyzed strands may be associated after generation of optical signatures, for example, by using molecular tags (which may be, for example, oligonucleotide segments attached to target polynucleotides in a known position, length and sequence pattern and diversity to permit ready association). As noted below, optical signature of the invention may comprise mixed optical signals in that the signal detected in each detection interval may comprise contributions from multiple optical labels emitting within a resolution limited area or volume; that is, they may (for example) be mixed FRET signals, as described by Huber et al, U.S. patent publication US20160076091, which is incorporated herein by reference.

As mentioned above, in some embodiments, methods of the invention may be implemented with the following steps: (a) copying a strand of a double stranded polynucleotide so that nucleotide analogs with distinct optical labels are substituted for at least two kinds of nucleotide to form a labeled strand; (b) copying a complement of the strand so that said nucleotide analogs are substituted for the same at least two kinds of nucleotide to form a labeled complement; (c) translocating the labeled stand through a nanopore so that the nucleotides of the labeled strand pass single file through a detection zone where optical labels are excited to generate optical signals; (d) quenching fluorescent signals from excited fluorescent labels outside of the detection zone; (e) detecting a time series of optical signals from the optical labels as the labeled strand translocates through the nanopore to produce a strand optical signature; (f) translocating the labeled complement through a nanopore so that the nucleotides of the labeled complement pass single file through an excitation zone where optical labels are excited to generate optical signals; (g) quenching fluorescent signals from excited fluorescent labels outside of the detection zone; (h) detecting a time series of optical signals from the optical labels as the labeled complement translocates through the nanopore to produce a complement optical signature; (i) determining a sequence of the double stranded polynucleotide from the strand optical signature and the complement optical signature. In some embodiments, two kinds of nucleotide are labeled, which may be C's and T's, C's and G's, C's and A's, T's and G's, T's and A's, or G's and A's. In some embodiments, pyrimidine nucleotides are labeled. In other embodiments, purine nucleotides are labeled. In some embodiments, selected kinds of nucleotides of a strand are labeled by incorporating labeled analog dNTPs of the selected kind of nucleotides in a primer extension reaction using a nucleic acid polymerase. In other embodiments, selected kinds of nucleotides of a strand are labeled by incorporating analog dNTPs of the selected kinds of nucleotides in an extension reaction, wherein the analog dNTPs are derivatized with orthogonally reactive functionalities that allow attachment of different labels to different kinds of nucleotides in a subsequent reaction. This latter labeling approach is disclosed in Jett et al, U.S. Pat. No. 5,405,747, which is incorporated herein by reference.

In some embodiments, three kinds of nucleotide are labeled, which may include labeling C's with a first optical label, T's with a second optical label, and G's and A's with a third optical label. In other embodiments, the following groups of nucleotides may be labeled as indicated: C's and G's with a first optical label and second optical label, respectively, and T's and A's with a third optical label; C's and A's with a first optical label and second optical label, respectively, and T's and G's with a third optical label; T's and G's with a first optical label and second optical label, respectively, and C's and A's with a third optical label; A's and G's with a first optical label and second optical label, respectively, and T's and C's with a third optical label.

In some embodiments, optical labels are fluorescent acceptor molecules that generate a fluorescent resonance energy transfer (FRET) signal after energy transfer from a donor associated with a nanopore. In some embodiments, as described further below, donors may be optically active nanoparticles, such as, quantum dots, nanodiamonds, or the like. Selection of particular combinations of acceptor molecules and donors are design choices for one of ordinary skill in the art. In some embodiments, some of which are described more fully below, a single quantum dot is attached to a nanopore and is excited to fluoresce using an excitation beam whose wavelength is sufficiently separated, usually lower (i.e. bluer), so that it does not contribute to FRET signals generated by acceptors. Likewise, a quantum dot is selected whose emission wavelength overlaps the absorption bands of both acceptor molecules to facilitate FRET interactions. In some embodiments, two donors may be used for each excitation zone of a nanopore, wherein the emission wavelength of each is selected to optimally overlap the absorption band of a different one of the acceptor molecules.

Figure 6A:
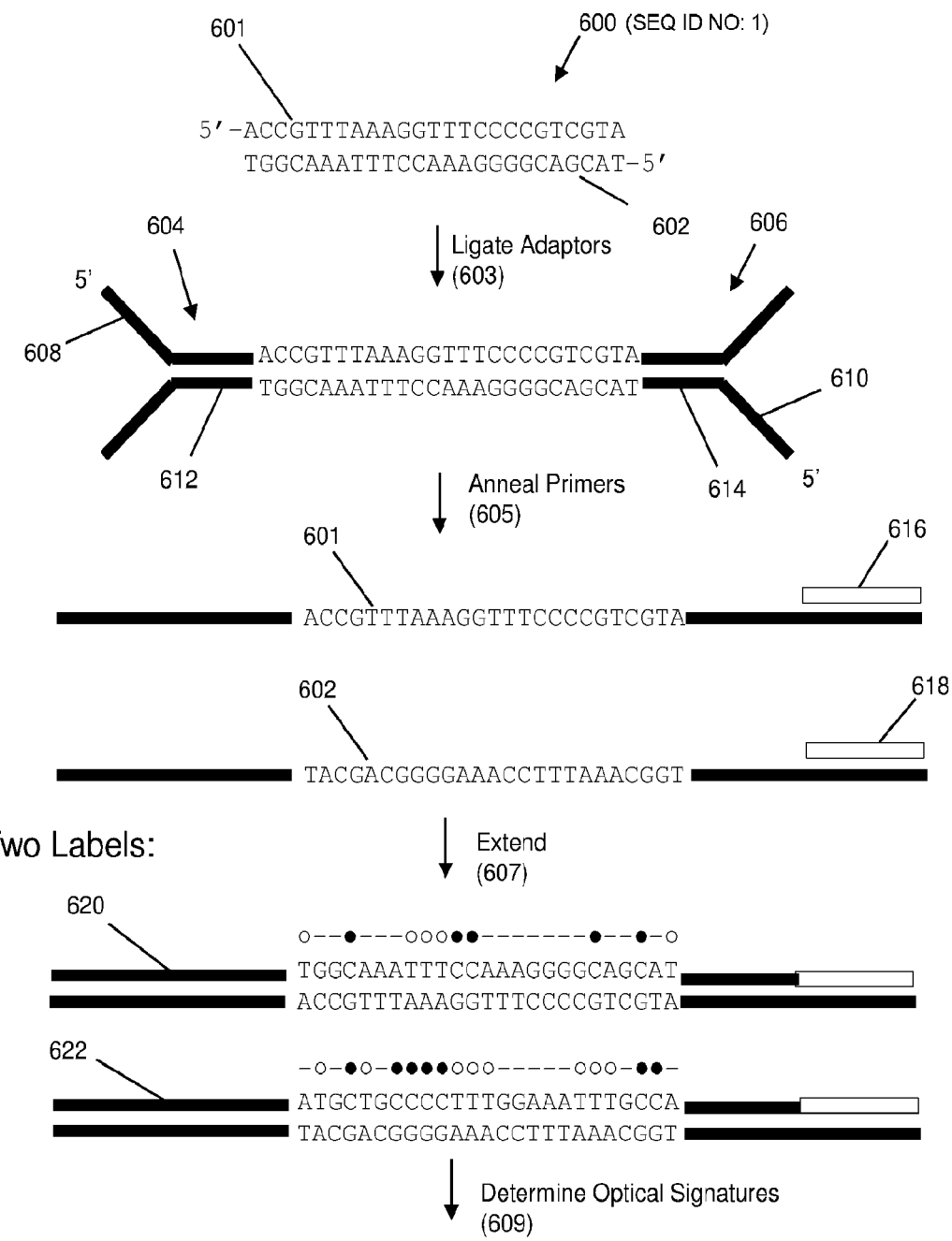
FIGS. 6A-6C illustrate embodiments employing two and three fluorescent labels.

In FIG. 6A, double stranded target polynucleotide (600) (SEQ ID NO: 1) consists of sense strand (601) and complementary antisense strand (602), to which is ligated (603) "Y" adaptors (604) and (606) using conventional methods, e.g. Weissman et al, U.S. Pat. No. 6,287,825; Schmitt et al, U.S. patent publication US2015/004468; which are incorporated herein by reference. Arms (608) and (610) of adaptors (604 and 606, respectively) include primer binding sites to which primers (616) and (618) are annealed (605). Double stranded portions (612) and (614) may include tag sequences, e.g. one or both may include randomers of predetermined length and composition, which may be used for later re-association of the strands, for example, to obtain sequence information from the respective optical signatures of the strands. After annealing primers (616) and (618), they may be extended (607) by a nucleic acid polymerase in the presence of (for example, as illustrated) labeled dUTP analogs (labels shown as open circles in the incorporated nucleotides) and labeled dCTP analogs (labels shown as filled circles in the incorporated nucleotides) and natural unlabeled dGTPs and dATPs (with neither unlabeled dTTP nor unlabeled dCTP being present so that the analogs are fully substituted in the extended strands). The absence of labels on G's and A's are illustrated as dashes above the incorporated nucleotides. In an ideal detection system without noise, the sequence of open circles, filled circles and dashes would be good representations of optical signatures generated by the indicated sense and antisense strands as they pass through an excitation zone of a nanopore.

Figure 6B:
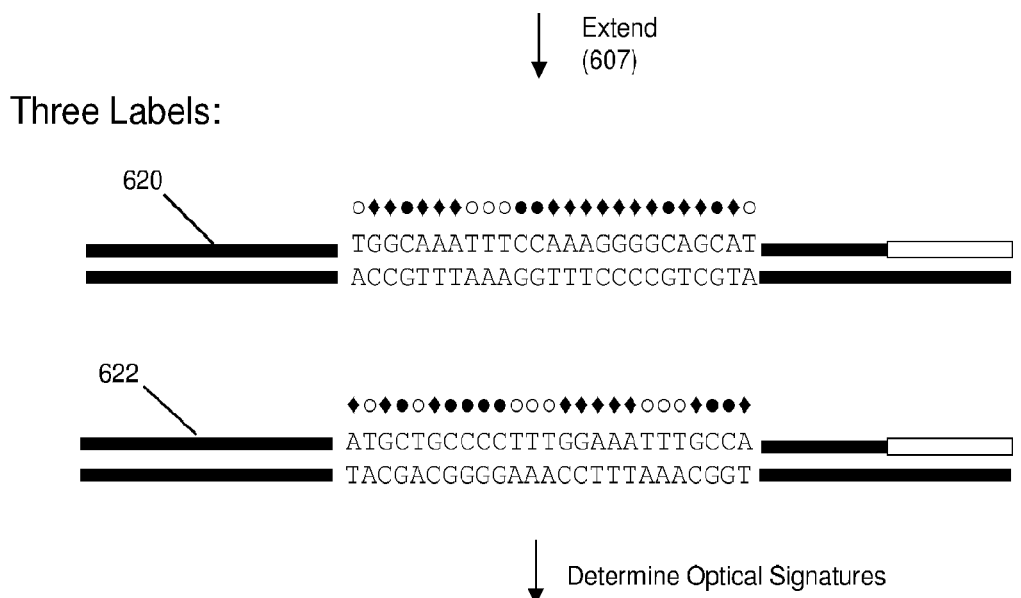

In FIG. 6B, extension products (620) and (622) are illustrated for an alternative embodiment employing three labels. Incorporated labeled dUTP analogs are shown as open circles and incorporated labeled dCTP analogs are shown as filled circles, as above. Incorporated labeled dATP and dGTP analogs are shown as filled diamonds.

Guidance in selecting the kinds of nucleotide to label, kinds of labels and linkers for attaching them to bases, and nucleic acid polymerases for extension reactions in the presence of dNTP analogs can be found in the following references, which are incorporated by reference: Goodman et al, U.S. Pat. No. 5,945,312; Jett et al, U.S. Pat. No. 5,405,747; Muehlegger et al, U.S. patent publication US2004/0214221; Giller et al, Nucleic Acids Research, 31(10): 2630-2635 (2003); Tasara et al, Nucleic Acids Research, 31(10): 2636-2646 (2003); Augustin et al, J. Biotechnology, 86: 289-301 (2001); Brakmann, Current Pharmacuetical Biotechnology, 5(1): 119-126 (2004); and the like. Exemplary nucleic acid polymerases for use with the invention include, but are not limited to, Vent exo$^-$, Taq, E. coli Pol I, Tgo exo$^-$, Klenow fragment exo$^-$, Deep Vent exo$^-$, and the like. In some embodiments, exemplary nucleic acid polymerases include, but are not limited to, Vent exo$^-$ and Klenow fragment exo$^-$. Exemplary fluorescent labels for dNTP analogs include, but are not limited to, Alexa 488, AMCA, Atto 655, Cy3, Cy5, Evoblue 30, fluorescein, Gnothis blue 1, Gnothis blue 2, Gnothis blue 3, Dy630, Dy635, MR121, rhodamine, Rhodamine Green, Oregon Green, TAMRA, and the like. Exemplary fluorescent labels for dUTP analogs include, but are not limited to, Alexa 488, AMCA, Atto 655, Cy3, Cy5, Dy630, Dy665, Evoblue 30, Evoblue 90, fluorescein, Gnothis blue 1, Gnothis blue 2, Gnothis blue 3, MR121, Oregon Green, rhodamine, Rhodamine Green, TAMRA, and the like. Exemplary fluorescent labels for dCTP analogs include, but are not limited to, Atto 655, Cy5, Evoblue 30, Gnothis blue 3, rhodamine, Rhodamine Green, TAMRA, and the like. Exemplary fluorescent labels for dATP analogs include, but are not limited to, Atto 655, Cy5, Evoblue 30, Gnothis blue 3, Rhodamine Green, and the like. Exemplary fluorescent labels for dGTP analogs include, but are not limited to, Evoblue 30, Gnothis blue 3, Rhodamine Green, and the like. Exemplary pairs of fluorescent labels for dUTP analogs and dCTP analogs include, but are not limited to, (TAMRA, Rhodamine Green), (Atto 655, Evoblue 30), (Evoblue 30, Atto 655), (Evoblue 30, Gnothis blue 3), (Evoblue 30, Rhodamine Green), (Gnothis blue 1, Rhodamine Green), (Gnothis blue 2, Atto 655), Gnothis blue 3, Cy5), and the like.

Figure 6C:
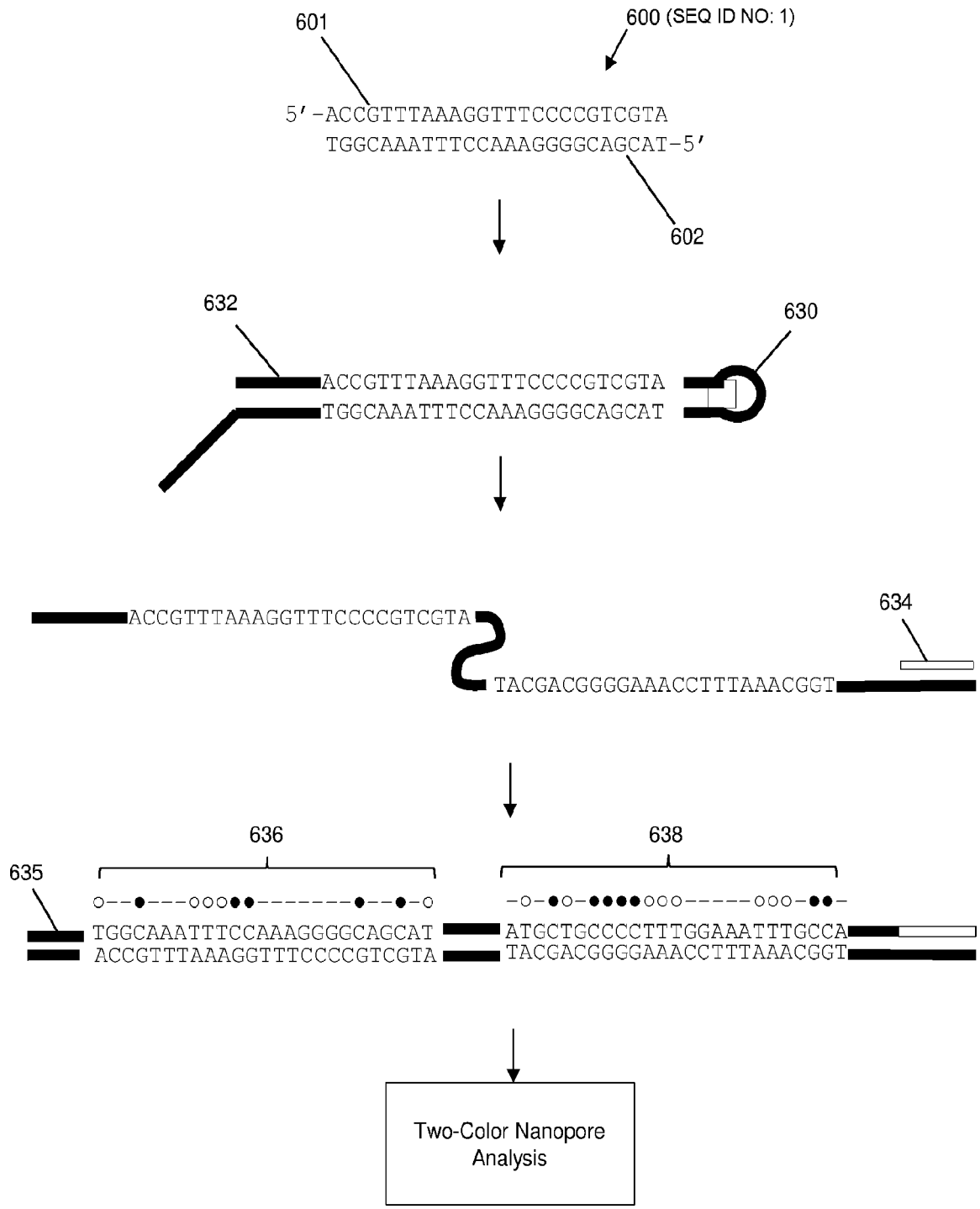

FIG. 6C illustrates an embodiment in which two labels are used and sense and antisense strands are linked by means of hairpin adaptor (630), for example, as taught in U.S. patent publications US 2015/0152492 and US 2012/0058468, which are incorporated herein by reference. Tailed adaptor (632) and hairpin adaptor (630) are ligated to target polynucleotide (600) (SEQ ID NO: 1). After denaturation and annealing of primer (634), an extension reaction produces extension product (635) which includes segment (636), the labeled complement of strand (601) and segment (638), the labeled reverse complement of strand (601). After translocation of extension product (635) through a nanopore and generation of an optical signature the sequence of target polynucleotide (600) (SEQ ID NO: 1) can be determined. Optionally, the sequence of hairpin (630) may be selected so that a predetermined pattern of labels is incorporated during the extension reaction, which may be used to assist in the analysis of the optical signature, e.g. by indicating where segment (636) ends and where segment (638) begins, or the like.

Nanopores and Nanopore Arrays

Nanopores used with the invention may be solid-state nanopores, protein nanopores, or hybrid nanopores comprising protein nanopores or organic nanotubes such as carbon or graphene nanotubes, configured in a solid-state membrane, or like framework. Important features of nanopores include constraining polynucleotide analytes, such as labeled polynucleotides so that their monomers pass through a signal generation region (or equivalently, an excitation zone, or detection zone, or the like) in sequence. That is, a nanopore constrains the movement of a polynucleotide analyte, such as a polynucleotide, so that nucleotides pass through a detection zone (or excitation region) in single file. In some embodiments, additional functions of nanopores include (i) passing single stranded nucleic acids while not passing double stranded nucleic acids, or equivalently bulky molecules and/or (ii) constraining fluorescent labels on nucleotides so that fluorescent signal generation is suppressed or directed so that it is not collected.

In some embodiments, nanopores used in connection with the methods and devices of the invention are provided in the form of arrays, such as an array of clusters of nanopores, which may be disposed regularly on a planar surface. In some embodiments, clusters are each in a separate resolution limited area so that optical signals from nanopores of different clusters are distinguishable by the optical detection system employed, but optical signals from nanopores within the same cluster cannot necessarily be assigned to a specific nanopore within such cluster by the optical detection system employed.

Solid state nanopores may be fabricated in a variety of materials including but not limited to, silicon nitride ($Si_3N_4$), silicon dioxide ($SiO_2$), and the like. The fabrication and operation of nanopores for analytical applications, such as DNA sequencing, are disclosed in the following exemplary references that are incorporated by reference: Ling, U.S. Pat. No. 7,678,562; Hu et al, U.S. Pat. No. 7,397,232; Golovchenko et al, U.S. Pat. No. 6,464,842; Chu et al, U.S. Pat. No. 5,798,042; Sauer et al, U.S. Pat. No. 7,001,792; Su et al, U.S. Pat. No. 7,744,816; Church et al, U.S. Pat. No. 5,795,782; Bayley et al, U.S. Pat. No. 6,426,231; Akeson et al, U.S. Pat. No. 7,189,503; Bayley et al, U.S. Pat. No. 6,916,665; Akeson et al, U.S. Pat. No. 6,267,872; Meller et al, U.S. patent publication 2009/0029477; Howorka et al, International patent publication WO2009/007743; Brown et al, International patent publication WO2011/067559; Meller et al, International patent publication WO2009/020682; Polonsky et al, International patent publication WO2008/092760; Van der Zaag et al, International patent publication WO2010/007537; Yan et al, Nano Letters, 5(6): 1129-1134 (2005); Iqbal et al, Nature Nanotechnology, 2: 243-248 (2007); Wanunu et al, Nano Letters, 7(6): 1580-1585 (2007); Dekker, Nature Nanotechnology, 2: 209-215 (2007); Storm et al, Nature Materials, 2: 537-540 (2003); Wu et al, Electrophoresis, 29(13): 2754-2759 (2008); Nakane et al, Electrophoresis, 23: 2592-2601 (2002); Zhe et al, J. Micromech. Microeng., 17: 304-313 (2007); Henriquez et al, The Analyst, 129: 478-482 (2004); Jagtiani et al, J. Micromech. Microeng., 16: 1530-1539 (2006); Nakane et al, J. Phys. Condens. Matter, 15 R1365-R1393 (2003); DeBlois et al, Rev. Sci. Instruments, 41(7): 909-916 (1970); Clarke et al, Nature Nanotechnology, 4(4): 265-270 (2009); Bayley et al, U.S. patent publication 2003/0215881; and the like.

In some embodiments, the invention comprises nanopore arrays with one or more light-blocking layers, that is, one or more opaque layers. Typically nanopore arrays are fabricated in thin sheets of material, such as, silicon, silicon nitride, silicon oxide, aluminum oxide, or the like, which readily transmit light, particularly at the thicknesses used, e.g. less than 50-100 nm. For electrical detection of analytes this is not a problem. However, in optically-based detection of labeled molecules translocating nanopores, light transmitted through an array invariably excites materials outside of intended reaction sites, thus generates optical noise, for example, from nonspecific background fluorescence, fluorescence from labels of molecules that have not yet entered a nanopore, or the like. In one aspect, the invention addresses this problem by providing nanopore arrays with one or more light-blocking layers that reflect and/or absorb light from an excitation beam, thereby reducing background noise for optical signals generated at intended reaction sites associated with nanopores of an array. In some embodiments, this permits optical labels in intended reaction sites to be excited by direct illumination. In some embodiments, an opaque layer may be a metal layer. Such metal layer may comprise Sn, Al, V, Ti, Ni, Mo, Ta, W, Au, Ag or Cu. In some embodiments such metal layer may comprise Al, Au, Ag or Cu. In still other embodiments, such metal layer may comprise aluminum or gold, or may comprise solely aluminum. The thickness of an opaque layer may vary widely and depends on the physical and chemical properties of material composing the layer. In some embodiments, the thickness of an opaque layer may be at least 5 nm, or at least 10 nm, or at least 40 nm. In other embodiments, the thickness of an opaque layer may be in the range of from 5-100 nm; in other embodiments, the thickness of an opaque layer may be in the range of from 10-80 nm. An opaque layer need not block (i.e. reflect or absorb) 100 percent of the light from an excitation beam. In some embodiments, an opaque layer may block at least 10 percent of incident light from an excitation beam; in other embodiments, an opaque layer may block at least 50 percent of incident light from an excitation beam.

Opaque layers or coatings may be fabricated on solid state membranes by a variety of techniques known in the art. Material deposition techniques may be used including chemical vapor deposition, electrodeposition, epitaxy, thermal oxidation, physical vapor deposition, including evaporation and sputtering, casting, and the like. In some embodiments, atomic layer deposition may be used, e.g. U.S. Pat. No. 6,464,842; Wei et al, Small, 6(13): 1406-1414 (2010), which are incorporated by reference.

In some embodiments, a 1-100 nm channel or aperture may be formed through a solid substrate, usually a planar substrate, such as a membrane, through which an analyte, such as single stranded DNA, is induced to translocate. In other embodiments, a 2-50 nm channel or aperture is formed through a substrate; and in still other embodiments, a 2-30 nm, or a 2-20 nm, or a 3-30 nm, or a 3-20 nm, or a 3-10 nm channel or aperture if formed through a substrate. The solid-state approach of generating nanopores offers robustness and durability as well as the ability to tune the size and shape of the nanopore, the ability to fabricate high-density arrays of nanopores on a wafer scale, superior mechanical, chemical and thermal characteristics compared with lipid-based systems, and the possibility of integrating with electronic or optical readout techniques. Biological nanopores on the other hand provide reproducible narrow bores, or lumens, especially in the 1-10 nanometer range, as well as techniques for tailoring the physical and/or chemical properties of the nanopore and for directly or indirectly attaching groups or elements, such as fluorescent labels, which may be FRET donors or acceptors, by conventional protein engineering methods. Protein nanopores typically rely on delicate lipid bilayers for mechanical support, and the fabrication of solid-state nanopores with precise dimensions remains challenging. In some embodiments, solid-state nanopores may be combined with a biological nanopore to form a so-called "hybrid" nanopore that overcomes some of these shortcomings, thereby providing the precision of a biological pore protein with the stability of a solid state nanopore. For optical read out techniques a hybrid nanopore provides a precise location of the nanopore which simplifies the data acquisition greatly.

In some embodiments, clusters may also be formed by disposing protein nanopores in lipid bilayers supported by solid phase membrane containing an array of apertures. For example, such an array may comprise apertures fabricated (e.g. drilled, etched, or the like) in solid phase support. The geometry of such apertures may vary depending on the fabrication techniques employed. In some embodiments, each such aperture is associated with, or encompassed by, a separate resolution limited area; however, in other embodiments, multiple apertures may be within the same resolution limited area. The cross-sectional area of the apertures may vary widely and may or may not be the same as between different clusters, although such areas are usually substantially the same as a result of conventional fabrication approaches. In some embodiments, apertures have a minimal linear dimension (e.g. diameter in the case of circular apertures) in the range of from 10 to 200 nm, or have areas in the range of from about 100 to $3 \times 10^4$ nm$^2$. Across the apertures may be disposed a lipid bilayer. The distribution of protein nanopores per aperture may be varied, for example, by controlling the concentration of protein nanopores during inserting step. In such embodiments, clusters of nanopores may comprise a random number of nanopores. In some embodiments, in which protein nanopores insert randomly into apertures, clusters containing one or more apertures on average have a number of protein nanopores that is greater than zero; in other embodiments, such clusters have a number of protein nanopores that is greater than 0.25; in other embodiments, such clusters have a number of protein nanopores that is greater than 0.5; in other embodiments, such clusters have a number of protein nanopores that is greater than 0.75; in other embodiments, such clusters have a number of protein nanopores that is greater than 1.0.

In some embodiments, methods and devices of the invention comprise a solid phase membrane, such as a SiN membrane, having an array of apertures therethrough providing communication between a first chamber and a second chamber (also sometimes referred to as a "cis chamber" and a "trans chamber") and supporting a lipid bilayer on a surface facing the second, or trans, chamber. In some embodiments, diameters of the aperture in such a solid phase membrane may be in the range of 10 to 200 nm, or in the range of 20 to 100 nm. In some embodiments, such solid phase membranes further include protein nanopores inserted into the lipid bilayer in regions where such bilayer spans the apertures on the surface facing the trans chamber. In some embodiments, such protein nanopores are inserted from the cis side of the solid phase membrane using techniques described herein. In some embodiments, such protein nanopores have a structure identical to, or similar to, α-hemolysin in that it comprises a barrel, or bore, along an axis and at one end has a "cap" structure and at the other end has a "stem" structure (using the terminology from Song et al, Science, 274: 1859-1866 (1996)). In some embodiments using such protein nanopores, insertion into the lipid bilayer results in the protein nanopore being oriented so that its cap structure is exposed to the cis chamber and its stem structure is exposed to the trans chamber.

In some embodiments, the present invention may employ hybrid nanopores in clusters, particularly for optical-based nanopore sequencing of polynucleotides. Such nanopores comprise a solid-state orifice, or aperture, into which a protein biosensor, such as a protein nanopore, is stably inserted. A charged polynucleotide may be attached to a protein nanopore (e.g. alpha hemolysin) by conventional protein engineering techniques after which an applied electric field may be used to guide a protein nanopore into an aperture in a solid-state membrane. In some embodiments, the aperture in the solid-state substrate is selected to be slightly smaller than the protein, thereby preventing it from translocating through the aperture. Instead, the protein will be embedded into the solid-state orifice.

Solid state, or synthetic, nanopores may be prepared in a variety of ways, as exemplified in the references cited above. In some embodiments a helium ion microscope may be used to drill the synthetic nanopores in a variety of materials, e.g. as disclosed by Yang et al, Nanotechnology, 22: 285310 (2011), which is incorporated herein by reference. A chip that supports one or more regions of a thin-film material, e.g. silicon nitride, that has been processed to be a free-standing membrane is introduced to the helium ion microscope (HIM) chamber. HIM motor controls are used to bring a free-standing membrane into the path of the ion beam while the microscope is set for low magnification. Beam parameters including focus and stigmation are adjusted at a region adjacent to the free-standing membrane, but on the solid substrate. Once the parameters have been properly fixed, the chip position is moved such that the free-standing membrane region is centered on the ion beam scan region and the beam is blanked. The HIM field of view is set to a dimension (in μm) that is sufficient to contain the entire anticipated nanopore pattern and sufficient to be useful in future optical readout (i.e. dependent on optical magnification, camera resolution, etc.). The ion beam is then rastered once through the entire field of view at a pixel dwell time that results in a total ion dose sufficient to remove all or most of the membrane autofluorescence. The field of view is then set to the proper value (smaller than that used above) to perform lithographically-defined milling of either a single nanopore or an array of nanopores. The pixel dwell time of the pattern is set to result in nanopores of one or more predetermined diameters, determined through the use of a calibration sample prior to sample processing. This entire process is repeated for each desired region on a single chip and/or for each chip introduced into the HIM chamber.

In some embodiments, a device for implementing the above methods for analyzing polynucleotides (such as single stranded polynucleotides) typically includes a set of electrodes for establishing an electric field across the layered membrane and nanopores. Single stranded nucleic acids are exposed to nanopores by placing them in an electrolyte in a first chamber, which is configured as the "cis" side of the layered membrane by placement of a negative electrode in the chamber. Upon application of an electric field, the negatively single stranded nucleic acids are captured by nanopores and translocated to a second chamber on the other side of the layered membrane, which is configured as the "trans" side of membrane by placement of a positive electrode in the chamber. The speed of translocation depends in part on the ionic strength of the electrolytes in the first and second chambers and the applied voltage across the nanopores. In optically based detection, a translocation speed may be selected by preliminary calibration measurements, for example, using predetermined standards of labeled single stranded nucleic acids that generate signals at different expected rates per nanopore for different voltages. Thus, for DNA sequencing applications, a translocation speed may be selected based on the signal rates from such calibration measurements. Consequently, from such measurements a voltage may be selected that permits, or maximizes, reliable nucleotide identifications, for example, over an array of nanopores. In some embodiments, such calibrations may be made using nucleic acids from the sample of templates being analyzed (instead of, or in addition to, predetermined standard sequences). In some embodiments, such calibrations may be carried out in real time during a sequencing run and the applied voltage may be modified in real time based on such measurements, for example, to maximize the acquisition of nucleotide-specific signals.

Optical Signal Detection

Figure 4:
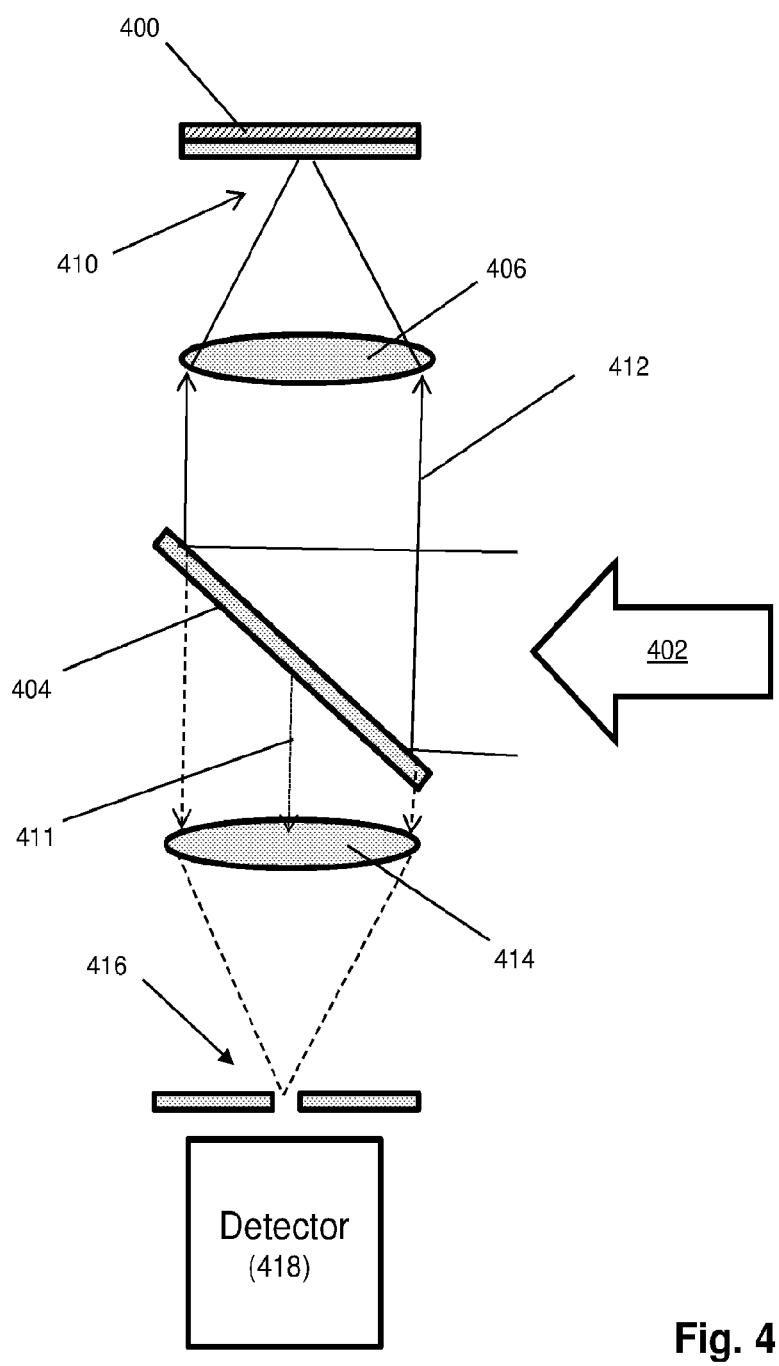
FIG. 4 illustrates the basic components of a confocal epi-illumination system.

In some embodiments, an epi-illumination system, in which excitation beam delivery and optical signal collection occurs through a single objective, may be used for direct illumination of labels on a polymer analyte or donors on nanopores. The basic components of a confocal epi-illumination system for use with the invention is illustrated in FIG. 4. Excitation beam (402) is directed to dichroic (404) and onto (412) objective lens (406) which focuses (410) excitation beam (402) onto layered membrane (400), in which labels are excited directly to emit an optical signal, such as a fluorescent signal, or are excited indirectly via a FRET interaction to emit an optical signal. Such optical signal is collected by objective lens (406) and directed to dichroic (404), which is selected so that it passes light of optical signal (411) but reflects light of excitation beam (402). Optical signal (411) passes through lens (414) which focuses it through pinhole (416) and onto detector (418). When optical signal (411) comprises fluorescent signals from multiple fluorescent labels further optical components, filters, beam splitters, monochromators, or the like, may be provided for further separating the different fluorescent signals from different fluorescent labels.

Figure 5:
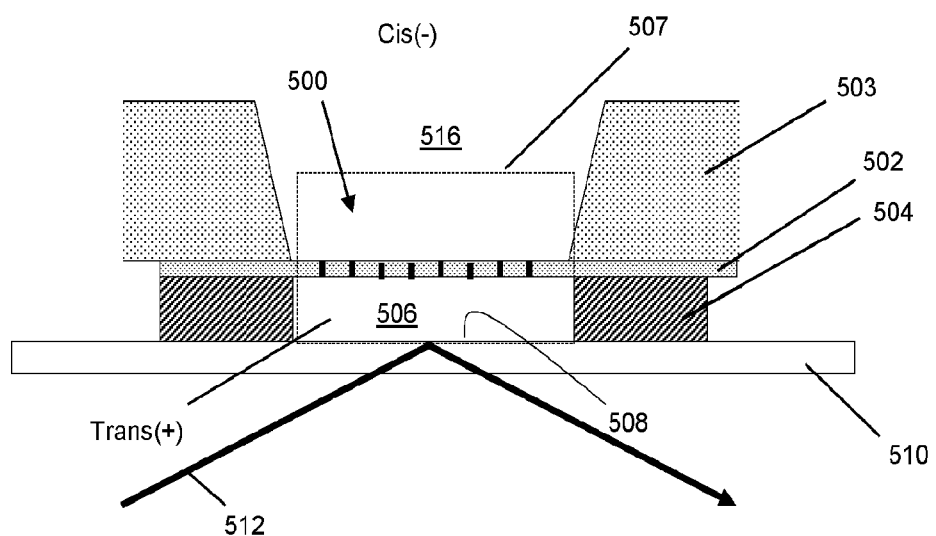
FIG. 5 illustrates elements of a TIRF system for excitation of optical labels in or near a nanopore array without FRET signal generation.

In some embodiments, labels on nucleotides may be excited by an evanescence field using an apparatus similar to that shown in FIG. 5, described in Soni et al, Review of Scientific Instruments, 81: 014301 (2010); and in U.S. patent publication 2012/0135410, which is incorporated herein by reference. In this apparatus, a very narrow second chamber on the trans side of a nanopore or nanopore array permits an evanescent field to extend from a surface of an underlying glass slide to establish detection zones both at entrances and exits of the nanopores, so that each optical measurement associated with a nanopore contains contributions from a plurality of labeled nucleotides. Array of apertures (500) (which may include protein nanopores inserted in a lipid bilayer), may be formed in silicon nitride layer (502), which may have a thickness in the range of from 20-100 nm. Silicon nitride layer (502) may be formed on a silicon support layer (503). Second chamber (506) may be formed by silicon nitride layer (502), silicon dioxide layer (504) which determines the height of second chamber (506), and surface (508) of glass slide (510). Silicon dioxide layer (504) may have a thickness in the range of from 50-100 nm. A desired evanescent field (507) extending from surface (508) across silicon nitride layer (502) may be established by directing light beam (512) at an appropriate angle relative to glass slide (510) so that TIR occurs. For driving labeled polynucleotide analytes through array (500), cis(−) conditions may be established in first chamber (516) and trans(+) conditions may be established in second chamber (506) with electrodes operationally connected to first and second chambers (506 and 521).

Definitions

"Evanescent field" means a non-propagating electromagnetic field; that is, it is an electromagnetic field in which the average value of the Poynting vector is zero.

"FRET" or "Förster, or fluorescence, resonant energy transfer" means a non-radiative dipole-dipole energy transfer mechanism from an excited donor fluorophore to an acceptor fluorophore in a ground state. The rate of energy transfer in a FRET interaction depends on the extent of spectral overlap of the emission spectrum of the donor with the absorption spectrum of the acceptor, the quantum yield of the donor, the relative orientation of the donor and acceptor transition dipoles, and the distance between the donor and acceptor molecules, Lakowitz, Principles of Fluorescence Spectroscopy, Third Edition (Springer, 2006). FRET interactions of particular interest are those which result a portion of the energy being transferred to an acceptor, in turn, being emitted by the acceptor as a photon, with a frequency lower than that of the light exciting its donor (i.e. a "FRET signal"). "FRET distance" means a distance between a FRET donor and a FRET acceptor over which a FRET interaction can take place and a detectable FRET signal produced by the FRET acceptor.

"Kit" refers to any delivery system for delivering materials or reagents for carrying out a method of the invention. In the context of reaction assays, such delivery systems include systems that allow for the storage, transport, or delivery of reaction reagents (e.g., fluorescent labels, such as mutually quenching fluorescent labels, fluorescent label linking agents, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second or more containers contain mutually quenching fluorescent labels.

"Nanopore" means any opening positioned in a substrate that allows the passage of analytes through the substrate in a predetermined or discernable order, or in the case of polymer analytes, passage of their monomeric units through the substrate in a predetermined or discernible order. In the latter case, a predetermined or discernible order may be the primary sequence of monomeric units in the polymer. Examples of nanopores include proteinaceous or protein based nanopores, synthetic or solid state nanopores, and hybrid nanopores comprising a solid state nanopore having a protein nanopore embedded therein. A nanopore may have an inner diameter of 1-10 nm or 1-5 nm or 1-3 nm. Examples of protein nanopores include but are not limited to, alpha-hemolysin, voltage-dependent mitochondrial porin (VDAC), OmpF, OmpC, MspA and LamB (maltoporin), e.g. disclosed in Rhee, M. et al., Trends in Biotechnology, 25(4) (2007): 174-181; Bayley et al (cited above); Gundlach et al, U.S. patent publication 2012/0055792; and the like, which are incorporated herein by reference. Any protein pore that allows the translocation of single nucleic acid molecules may be employed. A nanopore protein may be labeled at a specific site on the exterior of the pore, or at a specific site on the exterior of one or more monomer units making up the pore forming protein. Pore proteins are chosen from a group of proteins such as, but not limited to, alpha-hemolysin, MspA, voltage-dependent mitochondrial porin (VDAC), Anthrax porin, OmpF, OmpC and LamB (maltoporin). Integration of the pore protein into the solid state hole is accomplished by attaching a charged polymer to the pore protein. After applying an electric field the charged complex is electrophoretically pulled into the solid state hole. A synthetic nanopore, or solid-state nanopore, may be created in various forms of solid substrates, examples of which include but are not limited to silicones (e.g. Si3N4, SiO2), metals, metal oxides (e.g. Al2O3) plastics, glass, semiconductor material, and combinations thereof. A synthetic nanopore may be more stable than a biological protein pore positioned in a lipid bilayer membrane. A synthetic nanopore may also be created by using a carbon nanotube embedded in a suitable substrate such as but not limited to polymerized epoxy. Carbon nanotubes can have uniform and well-defined chemical and structural properties. Various sized carbon nanotubes can be obtained, ranging from one to hundreds of nanometers. The surface charge of a carbon nanotube is known to be about zero, and as a result, electrophoretic transport of a nucleic acid through the nanopore becomes simple and predictable (Ito, T. et al., Chem. Commun. 12 (2003): 1482-83). The substrate surface of a synthetic nanopore may be chemically modified to allow for covalent attachment of the protein pore or to render the surface properties suitable for optical nanopore sequencing. Such surface modifications can be covalent or non-covalent. Most covalent modification include an organosilane deposition for which the most common protocols are described: 1) Deposition from aqueous alcohol. This is the most facile method for preparing silylated surfaces. A 95% ethanol-5% water solution is adjusted to pH 4.5-5.5 with acetic acid. Silane is added with stirring to yield a 2% final concentration. After hydrolysis and silanol group formation the substrate is added for 2-5 min. After rinsed free of excess materials by dipping briefly in ethanol. Cure of the silane layer is for 5-10 min at 110 degrees Celsius. 2) Vapor Phase Deposition. Silanes can be applied to substrates under dry aprotic conditions by chemical vapor deposition methods. These methods favor monolayer deposition. In closed chamber designs, substrates are heated to sufficient temperature to achieve 5 mm vapor pressure. Alternatively, vacuum can be applied until silane evaporation is observed. 3) Spin-on deposition. Spin-on applications can be made under hydrolytic conditions which favor maximum functionalization and polylayer deposition or dry conditions which favor monolayer deposition. In some embodiments, single nanopores are employed with methods of the invention. In other embodiments, a plurality of nanopores are employed. In some of the latter embodiments, a plurality of nanopores is employed as an array of nanopores, usually disposed in a planar substrate, such as a solid phase membrane. Nanopores of a nanopore array may be spaced regularly, for example, in a rectilinear pattern, or may be spaced randomly. In a preferred embodiment, nanopores are spaced regularly in a rectilinear pattern in a planar solid phase substrate.

"Polymer" means a plurality of monomers connected into a linear chain. Usually, polymers comprise more than one type of monomer, for example, as a polynucleotide comprising A's, C's, G's and T's, or a polypeptide comprising more than one kind of amino acid. Monomers may include without limitation nucleosides and derivatives or analogs thereof and amino acids and derivatives and analogs thereof. In some embodiments, polymers are polynucleotides, whereby nucleoside monomers are connected by phosphodiester linkages, or analogs thereof.

"Polynucleotide" or "oligonucleotide" are used interchangeably and each mean a linear polymer of nucleotide monomers or analogs thereof. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references. Likewise, the oligonucleotide and polynucleotide may refer to either a single stranded form or a double stranded form (i.e. duplexes of an oligonucleotide or polynucleotide and its respective complement). It will be clear to one of ordinary skill which form or whether both forms are intended from the context of the terms usage.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference:

Dieffenbach, editor, PCR Primer: A Laboratory Manual, 2nd Edition (Cold Spring Harbor Press, New York, 2003).

"Resolution limited area" is an area of a surface of a nanopore or nanowell array within which individual features or light emission sources cannot be distinguished by an optical signal detection system. Without intending to be limited by theory, such resolution limited area is determined by a resolution limit (also sometimes referred to as a "diffraction limit" or "diffraction barrier") of an optical system. Such limit is determined by the wavelength of the emission source and the optical components and may be defined by $d=\lambda/NA$, where d is the smallest feature that can be resolved, $\lambda$ is the wavelength of the light and NA is the numerical aperture of the objective lens used to focus the light. Thus, whenever two or more nanopores are within a resolution limited area and two or more optical signals are generated at the respective nanopores, an optical detection system cannot distinguish or determine which optical signals came from which nanopore. In accordance with the invention, a surface of a nanopore array may be partitioned, or subdivided, into non-overlapping regions, or substantially non-overlapping regions, corresponding to resolution limited areas. The size of such subdivisions corresponding to resolution limited areas may depend on a particular optical detection system employed. In some embodiments, whenever light emission sources are within the visible spectrum, a resolution limited area is in the range of from 300 nm$^2$ to 3.0 µm$^2$; in; other embodiments, a resolution limited area is in the range of from 1200 nm$^2$ to 0.7 µm$^2$; in other embodiments, a resolution limited area is in the range of from $3 \times 10^4$ nm$^2$ to 0.7 µm$^2$, wherein the foregoing ranges of areas are in reference to a surface of a nanopore or nanowell array. In some embodiments, the visible spectrum means wavelengths in the range of from about 380 nm to about 700 nm.

"Sequence determination", "sequencing" or "determining a nucleotide sequence" or like terms in reference to polynucleotides includes determination of partial as well as full sequence information of the polynucleotide. That is, the terms include sequences of subsets of the full set of four natural nucleotides, A, C, G and T, such as, for example, a sequence of just A's and C's of a target polynucleotide. That is, the terms include the determination of the identities, ordering, and locations of one, two, three or all of the four types of nucleotides within a target polynucleotide. In some embodiments, the terms include the determination of the identities, ordering, and locations of two, three or all of the four types of nucleotides within a target polynucleotide. In some embodiments sequence determination may be accomplished by identifying the ordering and locations of a single type of nucleotide, e.g. cytosines, within the target polynucleotide "catcgc . . . " so that its sequence is represented as a binary code, e.g. "100101 . . . " representing "c-(not c)(not c)c-(not c)-c . . . " and the like. In some embodiments, the terms may also include subsequences of a target polynucleotide that serve as a fingerprint for the target polynucleotide; that is, subsequences that uniquely identify a target polynucleotide, or a class of target polynucleotides, within a set of polynucleotides, e.g. all different RNA sequences expressed by a cell.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

---

---

What is claimed is:

1. A method for determining a nucleotide sequence of a polynucleotide comprising the steps of:

translocating a polynucleotide through a bore of a nanopore at a translocation speed, wherein nucleotides of the polynucleotide are labeled with fluorescent labels such that, when exposed to fluorescence excitation light, fluorescent labels of nucleotides that are in free solution are substantially quenched, and fluorescent labels of nucleotides within the bore are constrained such that substantially no detectable fluorescent signal is generated by the fluorescent labels therein;

exciting the fluorescent label of each nucleotide upon exiting the nanopore and prior to being quenched by a preceding mutually quenching fluorescent label of the polynucleotide or by a quenching agent in the solution;

measuring a fluorescent signal generated by fluorescent labels of the nucleotides exiting the nanopore, wherein the translocation speed is selected so that a fluorescent label of an exiting nucleotide is quenched before it travels more than an inter-nucleotide distance from the nanopore; and determining a nucleotide sequence of the polynucleotide from a sequence of measured fluorescent signals.

2. The method of claim 1 wherein said step of measuring includes selecting said translocation speed based on the relative values of fluorescent intensities distributed among a plurality of optical detection channels.

3. The method of claim 2 wherein said plurality of optical detection channels includes at least one channel for an emission maximum of each fluorescent label.

4. A method of determining a nucleotide sequences of polynucleotides, the method comprising the steps of:

(a) translocating single stranded polynucleotides through nanopores at a translocation speed, wherein nucleotides of the single stranded polynucleotides are labeled with fluorescent labels such that, when exposed to fluorescence excitation light, fluorescent labels of adjacent nucleotides are in a mutually quenched state in free solution and wherein the nanopores force the fluorescent labels within the nanopore into a constrained state wherein substantially no detectable signal is generated;

(b) exciting the fluorescent labels of nucleotides upon exiting the nanopores and prior to being quenched by the label of an adjacent nucleotide;

(c) measuring fluorescent signals generated by the fluorescent labels exiting the nanopores and determining from the measured fluorescent signals whether a single fluorescent label contributes to the measured fluorescent signal or a plurality of fluorescent labels contributes to the measured fluorescent signal at each nanopore;

(d) reducing the translocation speed by a predetermined value whenever a measured fluorescent signal at a nanopore is generated by a plurality of fluorescent labels;

(e) repeating steps (a) through (d) until the translocation speed corresponds to substantially every measured fluorescent signal at each nanopore comprising fluorescence from substantially a single fluorescent label; and (f) identifying nucleotides of the translocating polynucleotides from measured fluorescent signals.

5. The method of claim 4 wherein said step of reducing comprises lowering a voltage potential across said nanopores.

6. The method of claim 4 wherein nucleotides of said polynucleotides are labeled with second members of a FRET pair, each second member producing a FRET signal indicative of the nucleotide to which it is attached, and wherein nucleotides of said polynucleotides pass in sequence by a first member of the FRET pair positioned adjacent to said nanopore so that each second member upon exiting said nanopore passes within a FRET distance of the first member of the FRET pair; and wherein said step of exciting includes exposing the first member to excitation energy of a first wavelength so that FRET occurs between the first and second members of the FRET pair within the FRET distance to generate a FRET signal of a second wavelength indicative of the nucleotide exiting said nanopore.

7. The method of claim 6 wherein said nanopore is disposed in a solid phase membrane and wherein said first member of said FRET pair is attached to the solid phase membrane adjacent to said nanopore.

8. The method of claim 6 wherein said nanopore is a protein nanopore and wherein said first member of said FRET pair is attached to the protein nanopore.

9. The method of claim 6 wherein said first member of said FRET pair is a donor and said second member of said FRET pair is an acceptor.

10. The method of claim 9 wherein said donor is a quantum dot.

11. The method of claim 9 wherein said acceptor is a fluorescent organic dye.

* * * * *